(12) United States Patent
Silverman et al.

(10) Patent No.: US 11,993,569 B2
(45) Date of Patent: May 28, 2024

(54) 3-AMINO-4-HALOCYCLOPENTENE CARBOXYLIC ACIDS AS INACTIVATORS OF AMINOTRANSFERASES

(71) Applicant: Northwestern University, Evanston, IL (US)

(72) Inventors: Richard B. Silverman, Winnetka, IL (US); Sida Shen, Chicago, IL (US)

(73) Assignee: Northwestern University, Evanston, IL (US)

( * ) Notice: Subject to any disclaimer, the term of this patent is extended or adjusted under 35 U.S.C. 154(b) by 597 days.

(21) Appl. No.: 17/155,706

(22) Filed: Jan. 22, 2021

(65) Prior Publication Data

US 2021/0238120 A1    Aug. 5, 2021

Related U.S. Application Data

(60) Provisional application No. 62/964,962, filed on Jan. 23, 2020.

(51) Int. Cl.
*C07C 61/20*    (2006.01)
(52) U.S. Cl.
CPC .................................. *C07C 61/20* (2013.01)
(58) Field of Classification Search
CPC ...................................................... C07C 61/20
See application file for complete search history.

(56) References Cited

U.S. PATENT DOCUMENTS

| | | | |
|---|---|---|---|
| 9,670,141 | B2 | 6/2017 | Silverman |
| 9,856,231 | B2 | 1/2018 | Silverman |
| 9,993,449 | B2 | 6/2018 | Silverman |
| 10,189,807 | B2 | 1/2019 | Silverman |
| 10,800,753 | B2 | 10/2020 | Silverman |
| 10,822,301 | B2 | 11/2020 | Silverman |
| 10,836,708 | B2 | 11/2020 | Silverman |
| 11,078,153 | B2 | 8/2021 | Silverman |
| 11,203,596 | B2 | 12/2021 | Silverman |
| 2015/0196522 | A1 | 7/2015 | Silverman |
| 2016/0264544 | A1 | 9/2016 | Silverman |
| 2017/0239202 | A1 | 8/2017 | Silverman |
| 2018/0051001 | A1 | 2/2018 | Silverman |

(Continued)

FOREIGN PATENT DOCUMENTS

WO    2016073983 A1    5/2016

OTHER PUBLICATIONS

Bey, P. et al. Synthesis of (E)-4-amino-2,5-hexadienoic acid and (E)-4-amino-5-fluoro-2-pentenoic acid—irreversible inhibitors of 4-aminobutyrate-2-oxoglutarate aminotransferase. J. Org. Chem. 1986, 51, 2835-2838.

(Continued)

*Primary Examiner* — Theodore R. Howell
*Assistant Examiner* — Britt N Thomas
(74) *Attorney, Agent, or Firm* — Quarles & Brady LLP

(57) ABSTRACT

Disclosed are cyclopentene compounds for use as inhibitors of aminotransferases such as gamma-aminobutyric acid (GABA) aminotransferase (AT) and/or ornithine aminotransferase (OAT). The disclosed cyclopentene compounds include 3-amino-4-halocyclopente carboxylic acid compounds which may be formulated in pharmaceutical composition for treating diseases and disorders associated with GABA-AT and/or OAT activity, including epilepsy, addiction, hepatocellular carcinoma (HCC), and non-small cell lung cancer (NSCLC).

28 Claims, 7 Drawing Sheets

(56) References Cited

U.S. PATENT DOCUMENTS

| | | |
|---|---|---|
| 2018/0098952 A1 | 4/2018 | Silverman |
| 2018/0271816 A1 | 9/2018 | Silverman |
| 2019/0256489 A1 | 8/2019 | Silverman |
| 2019/0315677 A1 | 10/2019 | Silverman |
| 2019/0359555 A1 | 11/2019 | Silverman |
| 2020/0299296 A1 | 9/2020 | Silverman |
| 2020/0317606 A1 | 10/2020 | Silverman |
| 2021/0139412 A1 | 5/2021 | Silverman |
| 2021/0238120 A1 | 8/2021 | Silverman |

OTHER PUBLICATIONS

Bournaud, C. et al. Skeletal rearrangements in the 2,3-diazanorbornene series. A fast access to highly functionalized cyclopentanes. Org. Lett. 2006, 8, 3041-3043.

Boyd, S., Molecular operating environment. Chem. World-Uk 2005, 2, 66.

Christensen, E. M. et al. Resolving the cofactor-binding site in the proline biosynthetic enzyme human pyrroline-5-carboxylate reductase 1. J. Biol. Chem. 2017, 292, 7233-7243.

Churchich, J. E. et al. 4-Aminobutyrate aminotransferase—the presence of nonequivalent binding-sites. J. Biol. Chem. 1981, 256, 1101-1104.

Doumlele, K. et al. A case report on the efficacy of vigabatrin analogue (1S, 3S)-3-amino-4-difluoromethylenyl-1-cyclopentanoic acid (CPP-115) in a patient with infantile spasms. Epilepsy Behav. Case Rep. 2016, 6, 67-69.

Heath, T. K. et al. Practical spectrophotometric assay for the dapE-encoded N-succinyl-L, L-diaminopimelic acid desuccinylase, a potential antibiotic target. Plos One 2018, 13.

Hwang, B. Y. et al. Revisit of aminotransferase in the genomic era and its application to biocatalysis. J. Mol. Catal. B-Enzym. 2005, 37, 47-55.

Jansonius, J. N., Structure, evolution and action of vitamin B6-dependent enzymes. Curr. Opin. Struct. Biol. 1998, 8, 759-769.

Juncosa, J. I. et al., Design and mechanism of (S)-3-amino-4-(difluoromethylenyl)cyclopent-1-ene-1-carboxylic acid, a highly potent gamma-aminobutyric acid aminotransferase inactivator for the treatment of addiction. J. Am. Chem. Soc. 2018, 140, 2151-2164.

Juncosa, J. I. et al., Two continuous coupled assays for ornithine-delta-aminotransferase. Anal. Biochem. 2013, 440, 145-149.

Katagiri, N. et al. A highly efficient synthesis of the antiviral agent (+)-cyclaradine involving the regioselective cleavage of epoxide by neighboring participation. Tetrahedron Lett. 1997, 38, 1961-1964.

Krauss, G.; et al. Sabril(R) registry 5-year results: Characteristics of adult patients treated with vigabatrin. Epilepsy Behav. 2016, 56, 15-19.

Lee, H. et al., Mechanism of inactivation of gamma-aminobutyric acid aminotransferase by (1S,3S)-3-amino-4-difluoromethylene-1-cyclopentanoic acid (CPP-115). J. Am. Chem. Soc. 2015, 137, 2628-2640.

Lee, H. et al., Ornithine aminotransferase versus GABA aminotransferase: implications for the design of new anticancer drugs. Med. Res. Rev. 2015, 35, 286-305.

Lu, H. et al. Fluorinated conformationally restricted gamma-aminobutyric acid aminotransferase inhibitors. J. Med. Chem. 2006, 49, 7404-7412.

Maeda, S. et al. Intrinsic reaction coordinate: Calculation, bifurcation, and automated search. Int. J. Quantum Chem. 2015, 115, 258-269.

Mascarenhas, R., et al. "Selective targeting by a mechanism-based inactivator against pyridoxal 5'-phosphate-dependent enzymes: Mechanisms of inactivation and alternative turnover." Biochemistry 56.37 (2017): 4951-4961.

Meldrum, B. S. et al. Anticonvulsant action in mice with sound-induced seizures of the optical isomers of gamma-vinyl GABA. Eur. J. Pharmacol. 1983, 89, 149-152.

Moschitto, M. J. et al. Mechanism of inactivation of ornithine aminotransferase by (1S,3S)-3-amino-4-(hexafluoropropan-2-ylidenyl)cyclopentane-1-carboxylic acid. J. Am. Chem. Soc. 2019, 141, 10711-10721.

Nanavati, S. M. et al. Mechanisms of inactivation of gamma-aminobutyric-acid aminotransferase by the antiepilepsy drug gamma-vinyl gaba (vigabatrin). J. Am. Chem. Soc. 1991, 113, 9341-9349.

Pan, Y. et al. (1S, 3S)-3-Amino-4-difluoromethylenyl-1-cyclopentanoic acid (CPP-115), a potent gamma-aminobutyric acid aminotransferase inactivator for the treatment of cocaine addiction. J. Med. Chem. 2012, 55, 357-366.

Qiu, J. et al. A new class of conformationally rigid analogues of 4-amino-5-halopentanoic acids, potent inactivators of gamma-aminobutyric acid aminotransferase. J. Med. Chem. 2000, 43, 706-720.

Shen et al., "Mechanism-Based Design of 3-Amino-4-Halocyclopentenecarboxylic Acids as Inactivators of GABA Aminotransferase", ACS Med. Chem. Lett. 2020, 11, 10, 1949-1955.

Silverman, R. B., Design and mechanism of GABA aminotransferase inactivators. treatments for epilepsies and addictions. Chem. Rev. 2018, 118, 4037-4070.

Silverman, R. B., The 2011 E. B. Hershberg award for important discoveries in medicinally active substances: (1S,3S)-3-amino-4-difluoromethylenyl-1-cyclopentanoic acid (CPP-115), a GABA aminotransferase inactivator and new treatment for drug addiction and infantile spasms. J. Med. Chem. 2012, 55, 567-575.

Silverman, R. B., The potential use of mechanism-based enzyme inactivators in medicine. J. Enzyme Inhib. 1988, 2, 73-90.

Storici, P. et al. Mechanistic crystallography. Mechanism of inactivation of gamma-aminobutyric acid aminotransferase by (1R,3S,4S)-3-amino-4-fluorocyclopentane-1-carboxylic acid as elucidated by crystallography. Biochemistry 2004, 43, 14057-14063.

Strelow, J. M., A perspective on the kinetics of covalent and irreversible inhibition. SLAS Discov. 2017, 22, 3-20.

Vilar, S. et al. Medicinal chemistry and the molecular operating environment (MOE): application of QSAR and molecular docking to drug discovery. Curr. Top. Med. Chem. 2008, 8, 1555-1572.

Walters, D. C. et al. Metabolomic analyses of vigabatrin (VGB)-treated mice: GABA-transaminase inhibition significantly alters amino acid profiles in murine neural and non-neural tissues. Neurochem. Int. 2019, 125, 151-162.

Wang, Z. et al. "Syntheses and evaluation of fluorinated conformationally restricted analogues of GABA as potential Inhibitors of GABA aminotransferase." Bioorganic & medicinal chemistry 14.7 (2006): 2242-2252.

Wild, J. M. et al. Objective derivation of the morphology and staging of visual field loss associated with long-term vigabatrin therapy. CNS Drugs 2019, 33, 817-829.

Yogeeswari, P. et al. The GABA shunt: an attractive and potential therapeutic target in the treatment of epileptic disorders. Curr. Drug Metab. 2005, 6, 127-139.

A

B vigabatrin (1)
FDA approved

CPP-115 (2)
Phase I

OV329 (3)
Preclinical

FCP (4)

5

US 11,993,569 B2

3-AMINO-4-HALOCYCLOPENTENE CARBOXYLIC ACIDS AS INACTIVATORS OF AMINOTRANSFERASES

CROSS-REFERENCE TO RELATED PATENT APPLICATIONS

This application claims the benefit of priority under 35 U.S.C. § 119(e) to U.S. Provisional Application No. 62/964,962, filed on Jan. 23, 2020, the content of which is incorporated by reference in its entirety.

STATEMENT REGARDING FEDERALLY SPONSORED RESEARCH OR DEVELOPMENT

This invention was made with government support under R01DA030604 awarded by the National Institutes of Health. The government has certain rights in the invention.

BACKGROUND

The field of the invention relates to cyclopentene compounds for use as inhibitors of aminotransferases such as gamma-aminobutyric acid (GABA) aminotransferase (AT) and/or ornithine aminotransferase (OAT). In particular, the field of the invention relates to 3-amino-4-halocyclopentene carboxylic acid for use as inhibitors of aminotransferases such as GABA-AT and/or OAT, which are formulated as pharmaceutical compositions for treatment of epilepsy, addiction, hepatocellular carcinoma (HCC), non-small cell lung cancer (NSCLC), and other cancer cell lines that overexpress OAT.

Aminotransferases (ATs) are essential enzymes that catalyze two coupled transamination reactions between an amino acid and an α-keto acid, thus playing an important role in nitrogen metabolism in cells. All ATs require pyridoxal 5'-phosphate (PLP) as a cofactor, which is linked to a basic lysine residue in the catalytic pocket through a Schiff base, to convert an amino acid into the corresponding carbonyl compound with concomitant conversion of PLP into pyridoxamine 5'-phosphate (PMP) in the first half-reaction. In the second half-reaction, ATs catalyze the reaction of PMP with an acceptor α-keto acid to perform another transfer of an amino group, thereby converting PMP back to PLP.[1, 2] Recent findings have demonstrated that pharmacological inhibition of certain ATs (e.g., γ-aminobutyric acid AT and ornithine AT) is a therapeutic strategy aimed to treat neurological disorders and cancers, respectively.[3, 4]

γ-Aminobutyric acid aminotransferase (GABA-AT, E.C. 2.6.1.19) catalyzes the degradation of the prime inhibitory neurotransmitter GABA to succinic semialdehyde (SSA) with the generation of the major excitatory neurotransmitter L-glutamate (L-Glu) from α-ketoglutarate (α-KG).[4] Normal functioning of the central nervous system (CNS) requires well-balanced levels of inhibitory and excitatory neurotransmitters; a reduction in the level of GABA has been implicated in the symptoms associated with epilepsy,[5] suggesting that modulation of the deficient level of GABA in the CNS might produce an anticonvulsant effect. Among various approaches to increase the brain concentrations of GABA (e.g., GABA prodrugs and glutamic acid decarboxylase (GAD) activators),[4] mechanism-based inactivators (MBIs) of GABA-AT are attractive because of their unique inactivation mechanisms and their successful advancement into preclinical/clinical stages.[4] Unlike other irreversible inhibitors, MBIs are unreactive prior to conversion into an active species in the catalytic site of the target enzyme, thus minimizing unwanted off-target effects.[6]

Vigabatrin (Sabril®), a MBI of GABA-AT, exhibits anticonvulsant activity and was approved by the FDA in 2009 as an adjunctive therapy for refractory partial seizures.[7] Mechanistic studies revealed that it irreversibly inhibits GABA-AT by covalent modification through two different mechanisms, a Michael addition pathway (70%) and an enamine pathway (30%), leading to its anticonvulsant effect[8, 9] It was also found to prevent cocaine addiction at a dose of 300 mg/kg in a rat model.[10] However, there are considerable concerns regarding the permanent visual damage associated with long-term vigabatrin administration, which results because of its low inactivation efficiency and poor blood-brain barrier (BBB) permeability, which demand high daily doses (1-3 g per day) that eventually impair its clinical profile.[11, 12] Recent findings identified cyclopentane-based analogue CPP-115 and cyclopentene-based analogue OV329, which exhibit several hundred-fold improved inactivation efficiency relative to vigabatrin.[13, 14] GABA-AT crystal structures in complex with CPP-115/OV329 demonstrated that their difluoromethylenyl groups are converted into a carboxylate group in the binding site, and both compounds inactivate the enzyme via tight electrostatic interactions between the two carboxylate groups and two arginine residues (Arg192 and Arg445).[14, 15] CPP-115 has been investigated in a Phase I clinical trial[10] and as a compassionate use medication[16] as a treatment for infantile spasms, while OV329 suppressed the release of brain dopamine at a dose of 0.1 mg/kg in a rat model of cocaine addiction.[14] Therefore, mechanism-based inactivation of GABA-AT has served as an effective approach to discover novel therapeutic treatments for different neurological disorders.

In 2000, (1R,3S,4S)-3-amino-4-fluorocyclopentane carboxylic acid (FCP) was reported as an inactivator of GABA-AT.[17] In 2004, crystallography with GABA-AT revealed that FCP covalently modifies the Lys329-PLP linkage by forming imine adduct M5 derived from an enamine inactivation mechanism.[18] The proposed inactivation mechanism of FCP is initiated by FCP acting as a substrate to form Schiff base M1 with PLP, followed by deprotonation (M2) and subsequent elimination of fluoride ion to afford the imine intermediate (M3). Subsequent Lys329 attack at the imine moiety of M3 releases the enamine metabolite (M4) and PLP is returned to Lys329. M4 covalently modifies the Lys329-PLP complex to generate adduct M5 via an enamine mechanism. However, except for the co-crystal structure, its mechanism was not well supported. As a result, the search for an alternative to FCP in the treatment of epilepsy has been an ongoing concern in the art.

Another pyridoxal 5'-phosphate (PLP)-dependent enzyme belonging to the same evolutionary subgroup as GABA-AT is the enzyme ornithine aminotransferase (OAT). These two enzymes share a high structural homology and, like all aminotransferases, also have very similar catalytic mechanisms. OAT is expressed in many tissues, including liver, kidney, small intestine, brain, and eye and catalyzes the reversible conversion of ornithine and α-ketoglutarate to L-glutamate semialdehyde which cyclizes to $\delta_1$-pyrroline-5-carboxylate and L-glutamate. L-glutamate is then converted by glutamine synthetase to L-glutamine. Glutamine is the most abundant free amino acid in the body; it is essential for growth of both normal and neoplastic cells. However, tumor cells take up glutamine more efficiently than normal cells, and tumor growth is enhanced by glutamine. With respect to glutamine, cancer cells distinguish themselves from normal cells in that they have an increased requirement for glutamine to support anabolic processes that stimulate proliferation. Because of the structural similarities between OAT and GABA-AT, it has been shown that some inactivators of GABA-AT also inactivate OAT. Therefore, the compounds disclosed herein as inactivators of GABA-AT may also be used to modulate, reduce and/or inhibit OAT activity and may be useful in the treatment of malignant pathologic proliferative disorders, including but not limited to hepatocellular carcinoma (HCC) and non-small cell lung cancer (NSCLC).

SUMMARY

Disclosed are cyclopentene compounds, pharmaceutical compositions and methods of treating diseases or disorders associated with aminotransferase activity including gamma-aminobutyric acid aminotransferase (GABA-AT) activity and/or ornithine aminotransferase (OAT) activity. Diseases and disorders treated by the disclosed compounds, pharmaceutical compositions, and methods include neurological and psychological diseases and disorders such as epilepsy and addiction as well as cell proliferation diseases and disorders such as hepatocellular carcinoma (HCC), non-small cell lung cancer (NSCLC), and other cancer cell lines that overexpress OAT.

The disclosed cyclopentene compounds include derivatives of 3-amino-cyclopentene carboxylic acid. The disclosed compounds may have a formula as follows:

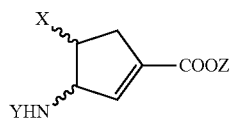

where: X is halo (e.g., F, Cl, Br, or I) or hydroxyl; Y is hydrogen or an amino-protecting group; and Z is hydrogen, alkyl, or a carboxyl protecting group, in which X and NHY can have either R- or S-stereochemistry. Also contemplated are salts of the disclosed compounds including pharmaceutically acceptable salts of the disclosed compounds. Also contemplated are zwitterion forms of the disclosed compounds.

Specifically, the disclosed compounds may have a formula:

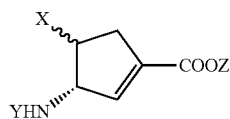

wherein X is halo (e.g., any of F, Cl, Br, and I) or hydroxyl having either R- or S-stereochemistry, Y is hydrogen or an amino-protecting group; and Z is hydrogen, alkyl, or a carboxyl protecting group. In some embodiments, the compound may be in the form of an ammonium salt having a counter ion that is the conjugate base of a protic acid.

The disclosed compounds may be formulated as pharmaceutical compositions comprising the compounds or pharmaceutically acceptable salts thereof in a pharmaceutically acceptable carrier for use in treatment methods for a subject in need thereof. In some embodiments, the disclosed compounds and pharmaceutical compositions may be utilized to treat diseases, disorders, or addictions associated with aminotransferases activity such as gamma-aminobutyric acid aminotransferase (GABA-AT) activity. Particularly, the disclosed compounds and pharmaceutical compositions may be utilized to modulate dopamine levels in a subject in need thereof. In some embodiments, the disclosed compounds and pharmaceutical compositions may be utilized to treat neurological or psychological disease or disorder in a subject in need thereof. Particularly, the disclosed compounds and pharmaceutical compositions may be utilized to treat substance addiction in a subject in need thereof.

The disclosed compounds and pharmaceutical compositions also may be utilized to treat a subject having a disease or disorder associated with ornithine aminotransferase (OAT) activity. Particularly, the disclosed compounds and pharmaceutical compositions may be utilized to modulate glutamine levels in a subject in need thereof. In some embodiments, the disclosed compounds and pharmaceutical compositions also may be utilized to treat cell proliferative diseases and disorders such as cancers, including but not limited to, hepatocellular carcinoma (HCC) and non-small cell lung cancer (NSCLC).

BRIEF DESCRIPTION OF THE FIGURES

FIG. 6. Inactivation efficiency of FCP versus 6a for GABA-AT.

DETAILED DESCRIPTION

Figure 1:
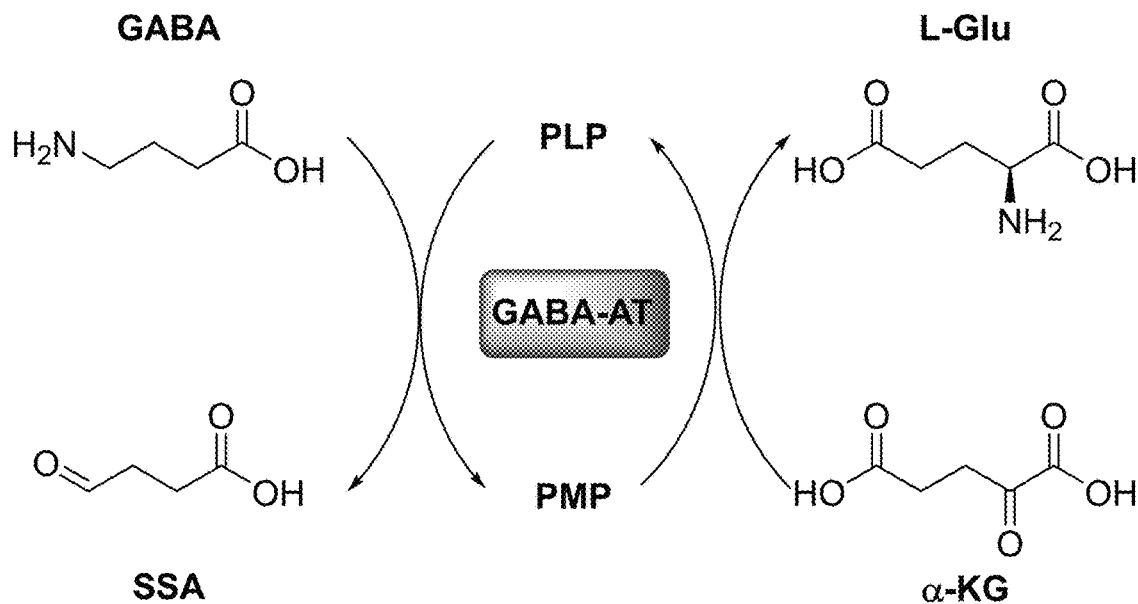
FIG. 1. Coupled transamination reactions of GABA-AT (A) and structures of MBI representatives 1-5 (B).
Figure 1:
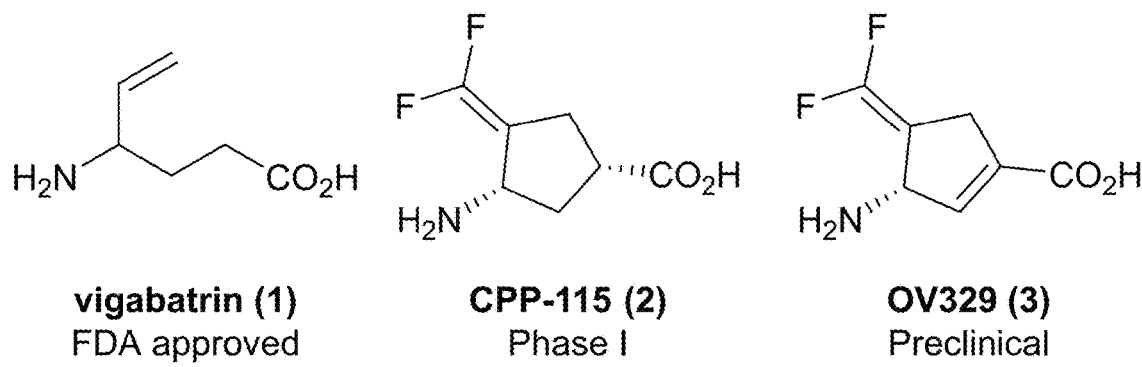
Figure 1:
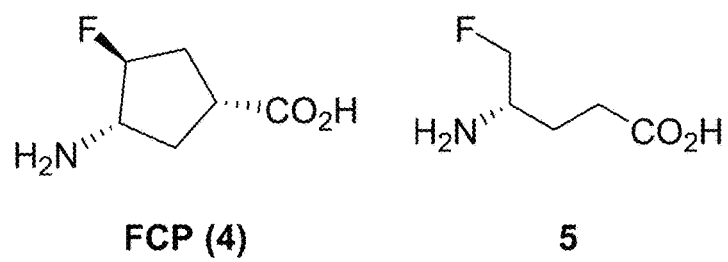

The present invention is described herein using several definitions, as set forth below and throughout the application.

Definitions

The disclosed subject matter may be further described using definitions and terminology as follows. The definitions and terminology used herein are for the purpose of describing particular embodiments only and are not intended to be limiting.

As used in this specification and the claims, the singular forms "a," "an," and "the" include plural forms unless the context clearly dictates otherwise. For example, the term "a substituent" should be interpreted to mean "one or more substituents," unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover, the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or "B" or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

A "subject in need thereof" as utilized herein refers to a subject in need of treatment for a disease, disorder, or addiction associated with aminotransferases activity such as gamma-amino butyric acid aminotransferase (GABA-AT) activity and/or ornithine aminotransferase (OAT) activity. The term "subject" may be used interchangeably with the terms "individual" and "patient" and includes human and non-human mammalian subjects.

Diseases and disorders associated with GABA-AT activity may include, but are not limited to, neurological and psychological diseases and disorders. Neurological disorders may include, but are not limited to epilepsy, partial seizures, complex partial seizures, secondary generalized seizures, tonic-clonic seizures, succinic semialdehyde dehydrogenase deficiency (SSADHD), infantile spasms in West's syndrome, Lennox-Gastaut syndrome, tubulous sclerosis, Tourette's syndrome, movement disorders, fibromyalgia, neuropathic pain, migraine related to epilepsy, restless leg syndrome and post-traumatic stress disorder, addiction, obesity, obsessive-compulsive disorders and Alzheimer's disease, and combinations thereof. Psychological disorders may include, but are not limited to, general anxiety disorder, pathological or compulsive gambling disorder, compulsive eating, body dysmorphic disorder, hypochondriasis, pathologic grooming conditions, kleptomania, pyromania, attention deficit hyperactivity disorder and impulse control disorders and combinations thereof.

Diseases and disorders associated with GABA-AT activity may include substance addiction. Substance addictions treated by the disclosed methods may include addictions to one or more of cocaine, heroin, alcohol, barbiturates, amphetamines, cannabis, methadone, opioids, stimulants, nicotine, and combinations thereof.

Diseases and disorder associated with OAT activity may include, but are not limited to, cell proliferative diseases and disorders such as cancers. Cancers may include, but are not limited to, hepatocellular carcinoma (HCC) and non-small cell lung cancer (NSCLC).

The disclosed compounds may be utilized to modulate enzyme activities including, but not limited to GABA-AT activity and OAT activity. The term "modulate" should be interpreted broadly to include "inhibiting" enzyme activity and/or otherwise modulating enzyme activity.

New Chemical Entities

New chemical entities may be disclosed herein and may be described using terms known in the art and defined herein.

The term "alkyl" as used herein refers to a saturated straight or branched hydrocarbon, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group. An exemplary alkylene group is —$CH_2CH_2$—.

The term "haloalkyl" refers to an alkyl group that is substituted with at least one halogen, for example, —$CH_2F$, —$CHF_2$, —$CF_3$, —$CH_2CF_3$, —$CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxyl" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively. A "cycloalkene" is a compound having a ring structure (e.g., of 3 or more carbon atoms) and comprising at least one double bond.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of a cycloalkyl group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number or ring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines, wherein substituents may include, for example, alkyl, cycloalkyl, heterocyclyl, alkenyl, and aryl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "carboxy" or "carboxyl" as used herein refers to the radical —COOH or its corresponding salts, e.g. —COONa, etc.

The term "amide" or "amido" or "carboxamido" as used herein refers to a radical of the form —R$^1$C(O)N(R$^2$)—, —R$^1$C(O)N(R$^2$) R$^3$—, —C(O)N R$^2$ R$^3$, or —C(O)NH$_2$, wherein R$^1$, R$^2$ and R$^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereo isomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise.

Pharmaceutical Compositions

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that modulates GABA-AT activity may be administered as a single compound or in combination with another compound that modulates GABA-AT or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds, which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counter-ion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated GABA-AT activity and/or OAT activity. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with GABA-AT activity and/or OAT activity.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

Transdermal patches can also be used to deliver the compounds. Transdermal patches can include a resinous composition in which the compound will dissolve or partially dissolve; and a film which protects the composition, and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

Cyclopentene Compounds and Uses Thereof

Disclosed herein are cyclopentene compounds, pharmaceutical compositions comprising the compounds, and methods of using the compounds and pharmaceutical compositions for treating diseases and disorders associated with aminotransferases activity such as GABA-AT activity and/or OAT activity. The disclosed cyclopentene compounds may include derivatives of 3-amino-cyclopentene carboxylic acid compounds or salts thereof having a formula as follows:

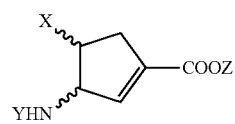

where:
X is halo (e.g., F, Cl, Br, or I) or hydroxyl; Y is hydrogen or an amino-protecting group; and Z is hydrogen, alkyl, or a carboxyl protecting group, in which X and NHY can have either R- or S-stereochemistry. Salts and hydrates of the disclosed compounds also are contemplated herein. Zwitterion forms of the disclosed compounds also are contemplated herein such as:

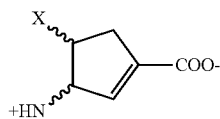

In some embodiments, the disclosed compounds may have a formula:

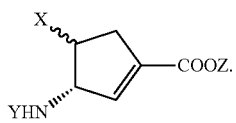

In some embodiments, the disclosed compounds may have a formula:

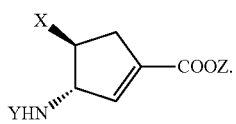

The disclosed compounds may include one or more protecting groups, including protecting groups for an amino group of the compounds and/or protecting groups for the carboxyl group of the compounds. In some embodiments, the disclosed compound has a formula:

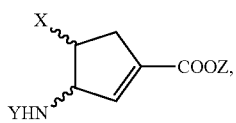

where Y is an amino-protecting group optionally selected from tert-butoxylcarbonyl (Boc), 9-fluorenylmethoxcarbonyl (FMoc), benzyloxycarbonyl or carboxybenzyl or carbobenzyloxy (Cbz), acetyl (Ac), trifluoroacetyl, phthalic anhydride, benzyl (Bn), benzoyl (Bz), triphenylmethyl (Tr), benzylidenyl, para-toluenesulfonyl (Ts). para-Methoxybenzyl carbonyl (Moz or MeOZ), para-Methoxybenzyl (PMB), 3,4-Dimethoxybenzyl (DMPM), p-methoxyphenyl (PMP), and trichloroethyl chloroformyl (Troc).

In other embodiments, the disclosed compounds have a formula:

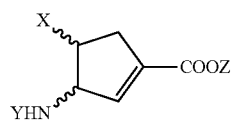

where Z is a protecting group optionally selected from alkyl such as methyl or tert-butyl; aryl such as benzyl; 2-6-disubstituted phenyls such as 2,6-dimethylphenol, 2,6-diisopropylphenol and 2,6-di-tert-butylphenol; and silyl.

In some embodiments, amino-protected and/or carboxyprotected compounds may include compounds having a formula selected from:

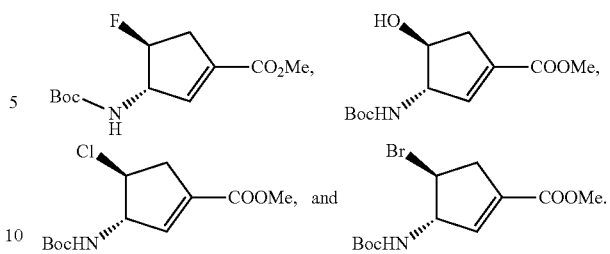

Specifically, the compounds disclosed herein may include compounds having a formula selected from:

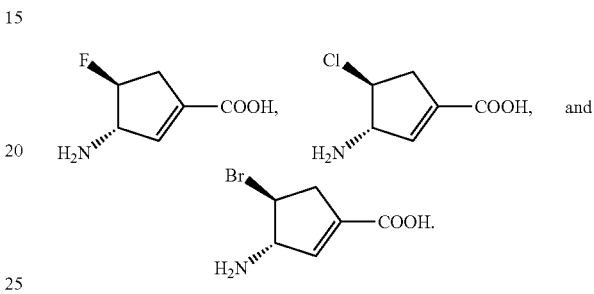

Salts of the disclosed compounds are contemplated herein. In some embodiments, the compound is an ammonium salt having a counter ion that is the conjugate base of a protic acid.

The disclosed compounds, salts thereof, and/or hydrates thereof may be formulated as pharmaceutical compositions comprising the compounds, salts thereof, and/or hydrates thereof, in a pharmaceutically acceptable carrier. The pharmaceutical compositions may be formulated for treating diseases or disorders associated with GABA-AT activity and/or OAT activity.

In some embodiments, the disclosed compounds and pharmaceutical compositions may be utilized for treating a subject having a disease, disorder, or addiction associated with gamma-aminobutyric acid aminotransferase (GABA-AT) activity, the method comprising administering to the subject the compounds and/or the pharmaceutical compositions. In these methods, the subject may be administered an amount of the compound sufficient to modulate GABA-AT activity.

In some embodiments, the disclosed compounds and pharmaceutical compositions may be utilized for modulating dopamine levels in a subject in need thereof. In these methods, the subject may be administered an amount of the compound sufficient to modulate GABA-AT activity. In these methods, the modulated dopamine levels may be responsive to ingestion of an addictive substance and preferably the method treats excessive dopamine release in the subject in response to ingestion of the addictive substance.

In some embodiments, the disclosed compounds and pharmaceutical compositions may be utilized for treating substance addiction in a subject in need thereof. In these methods, the subject may be administered an amount of the compound sufficient to modulate GABA-AT activity. In these methods, the subject may be addicted to a substance selected from, but not limited to, the group consisting of cocaine, heroin, alcohol, barbiturates, amphetamines, cannabis, methadone, opioids, stimulants, nicotine, and combinations thereof.

In some embodiments, the disclosed compounds and pharmaceutical compositions may be utilized for treating a neurological or psychological disease or disorder in a subject in need thereof. In these methods, the subject may be administered an amount of the compound sufficient to modulate GABA-AT activity. In these methods, the disease or disorder may be a neurological disorder optionally selected from the group consisting of, but not limited to, epilepsy, partial seizures, complex partial seizures, secondary generalized seizures, tonic-clonic seizures, succinic semialdehyde dehydrogenase deficiency (SSADHD), infantile spasms in West's syndrome, Lennox-Gastaut syndrome, tubulous sclerosis, Tourette's syndrome, movement disorders, fibromyalgia, neuropathic pain, migraine related to epilepsy, restless leg syndrome and post-traumatic stress disorder, addiction, obesity, obsessive-compulsive disorders and Alzheimer's disease, and combinations thereof. In these methods, the disease or disorder may be a psychological disorder optionally selected from, but not limited to, the group consisting of general anxiety disorder, pathological or compulsive gambling disorder, compulsive eating, body dysmorphic disorder, hypochondriasis, pathologic grooming conditions, kleptomania, pyromania, attention deficit hyperactivity disorder and impulse control disorders and combinations thereof.

In some embodiments, the disclosed compounds and pharmaceutical compositions are utilized in methods for treating a subject having a disease or disorder associated with ornithine aminotransferase (OAT) activity, the method comprising administering to the subject the compounds or the pharmaceutical compositions. In these methods, the subject may be administered an amount of the compound sufficient to modulate OAT activity. In these methods, the methods may reduce OAT activity and glutamate production characterized by OAT activity. These methods may be utilized for treating cell proliferative diseases and disorders including, but not limited to, cancers. In particular, the disclosed compounds and pharmaceutical compositions may be administered in methods for treating cancers, such as hepatocellular carcinoma (HCC) and non-small cell lung cancer (NSCLC).

ILLUSTRATIVE EMBODIMENTS

The following Embodiments are illustrative and are not intended to limit the scope of the claimed subject matter.

Embodiment 1. A compound having the following formula, a zwitterion form thereof, or a salt form thereof:

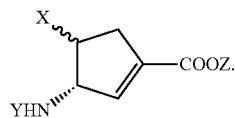

(I)

wherein X is halo (e.g., F, Cl, Br, or I) or hydroxyl; Y is hydrogen or an amino-protecting group; and Z is hydrogen, alkyl, or a carboxyl protecting group.

Embodiment 2. The compound of embodiment 1 having a formula:

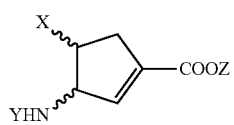

Embodiment 3. The compound of embodiment 1 or 2 having a formula:

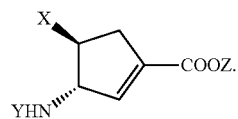

Embodiment 4. The compound of any of embodiments 1-3 having a formula:

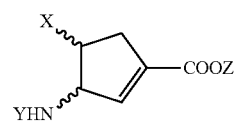

wherein Z is a carboxyl protecting group (e.g., alkyl such as methyl or tert-butyl, aryl such as benzyl, 2-6-disubstituted phenyls such as 2,6-dimethylphenol, 2,6-diisopropylphenol, and 2,6-di-tert-butylphenol, or silyl).

Embodiment 5. The compound of any of embodiments 1-4 having a formula:

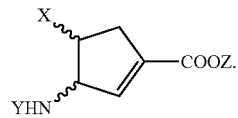

wherein Y is an amino-protecting group (e.g., tert-butoxylcarbonyl (Boc), 9-fluorenylmethoxcarbonyl (FMoc), benzyloxycarbonyl or carboxybenzyl or carbobenzyloxy (Cbz), acetyl (Ac), trifluoroacetyl, phthalic anhydride, benzyl (Bn), benzoyl (Bz), triphenylmethyl (Tr), benzylidenyl, para-toluenesulfonyl (Ts). para-Methoxybenzyl carbonyl (Moz or MeOZ), para-Methoxybenzyl (PMB), 3,4-Dimethoxybenzyl (DMPM), p-methoxyphenyl (PMP), and trichloroethyl chloroformyl (Troc)).

Embodiment 6. The compound of any of embodiments 1-5 having a formula selected from:

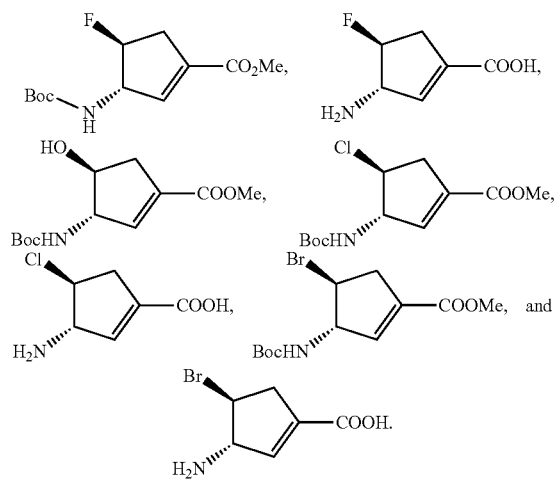

Embodiment 7. The compound of any of embodiments 1-6 in a salt form having a counter ion that is the conjugate base of a protic acid.

Embodiment 8. A pharmaceutical composition comprising any of the compound of any of embodiments 1-7 or pharmaceutically acceptable salts thereof in a pharmaceutically acceptable carrier.

Embodiment 9. A method of treating a subject having a disease, disorder, or addiction associated with gamma-aminobutyric acid aminotransferase (GABA-AT) activity, the method comprising administering to the subject the compound of any of embodiments 1-7 or the pharmaceutical composition of embodiment 8.

Embodiment 10. The method of embodiment 9, wherein the subject is administered an amount of the compound sufficient to modulate GABA-AT activity.

Embodiment 11. A method of modulating dopamine levels in a subject in need thereof, the method comprising administering to the subject the compound of any of embodiments 1-7 or the pharmaceutical composition of embodiment 8.

Embodiment 12. The method of embodiment 11, wherein the subject is administered an amount of the compound sufficient to modulate GABA-AT activity.

Embodiment 13. The method of embodiment 11 or 12, wherein the dopamine levels are responsive to ingestion of an addictive substance.

Embodiment 14. The method of any of embodiments 11-13, wherein the method treats excessive dopamine release in the subject.

Embodiment 15. A method for treating substance addiction in a subject in need thereof, the method comprising administering to the subject the compound of any of embodiments 1-7 or the pharmaceutical composition of embodiment 8.

Embodiment 16. The method of embodiment 15, wherein the subject is addicted to a substance selected from the group consisting of cocaine, heroin, alcohol, barbiturates, amphetamines, cannabis, methadone, opioids, stimulants, nicotine, and combinations thereof.

Embodiment 17. A method for treating a neurological or psychological disease or disorder in a subject in need thereof, the method comprising administering to the subject the compound of any of embodiments 1-7 or the pharmaceutical composition of embodiment 8.

Embodiment 18. The method of embodiment 17, wherein the subject is administered an amount of the compound sufficient to modulate GABA-AT activity.

Embodiment 19. The method of embodiment 17 or 18, wherein the disease or disorder is a neurological disorder selected from the group consisting of epilepsy, partial seizures, complex partial seizures, secondary generalized seizures, tonic-clonic seizures, succinic semialdehyde dehydrogenase deficiency (SSADHD), infantile spasms in West's syndrome, Lennox-Gastaut syndrome, tubulous sclerosis, Tourette's syndrome, movement disorders, fibromyalgia, neuropathic pain, migraine related to epilepsy, restless leg syndrome and post-traumatic stress disorder, addiction, obesity, obsessive-compulsive disorders and Alzheimer's disease, and combinations thereof.

Embodiment 20. The method of embodiment 17 or 18, wherein the disease or disorder is a psychological disorder selected from the group consisting of general anxiety disorder, pathological or compulsive gambling disorder, compulsive eating, body dysmorphic disorder, hypochondriasis, pathologic grooming conditions, kleptomania, pyromania, attention deficit hyperactivity disorder and impulse control disorders and combinations thereof.

Embodiment 21. A method of treating a subject having a disease or disorder associated with ornithine aminotransferase (OAT) activity, the method comprising administering to the subject the compound of any of embodiments 1-7 or the pharmaceutical composition of embodiment 8.

Embodiment 22. The method of embodiment 21, wherein the subject is administered an amount of the compound sufficient to modulate OAT activity.

Embodiment 23. The method of embodiment 21 or 22, wherein the method reduces OAT activity and glutamate production characterized by OAT activity.

Embodiment 24. The method of any of embodiments 21-23, wherein the disease or disorder is hepatocellular carcinoma (HCC), non-small cell lung cancer (NSCLC), or other diseases that involve overexpression of OAT.

EXAMPLES

The following Examples are illustrative and are not intended to limit the scope of the claimed subject matter.

Example 1

Reference is made to Shen and Silverman, "Mechanism-Based Design of 3-Amino-4-Halocyclopentenecarboxylic Acids as Inactivators of GABA Aminotransferase", *ACS Med. Chem. Lett.* 2020, 11, 10, 1949-1955, the content of which his incorporated by reference in entirety.

Title—Mechanism-Based Design of 3-Amino-4-Halocyclopentecarboxylic Acids as Inactivators of γ-Aminobutyric Acid Aminotransferase Aminotransferases (ATs) are essential enzymes that catalyze two coupled transamination reactions between an amino acid and an α-keto acid, thus playing an important role in nitrogen metabolism in cells. All ATs require pyridoxal 5'-phosphate (PLP) as a cofactor, which is linked to a basic lysine residue in the catalytic pocket through a Schiff base, to convert an amino acid into the corresponding carbonyl compound with concomitant conversion of PLP into pyridoxamine 5'-phosphate (PMP) in the first half-reaction. In the second half-reaction, ATs catalyze the reaction of PMP with an acceptor α-keto acid to perform another transfer of an amino group, thereby converting PMP back to PLP.[1, 2] Recent findings have demonstrated that pharmacological inhibition of certain ATs (e.g., γ-aminobutyric acid AT and ornithine AT) is a therapeutic strategy aimed to treat neurological disorders and cancers, respectively.[3, 4]

γ-Aminobutyric acid aminotransferase (GABA-AT, E.C. 2.6.1.19) catalyzes the degradation of the prime inhibitory neurotransmitter GABA to succinic semialdehyde (SSA) with the generation of the major excitatory neurotransmitter L-glutamate (L-Glu) from α-ketoglutarate (α-KG) (FIG. 1A).[4] Normal functioning of the central nervous system (CNS) requires well-balanced levels of inhibitory and excitatory neurotransmitters; a reduction in the level of GABA has been implicated in the symptoms associated with epilepsy,[5] suggesting that modulation of the deficient level of GABA in the CNS might produce an anticonvulsant effect. Among various approaches to increase the brain concentrations of GABA (e.g., GABA prodrugs and glutamic acid decarboxylase (GAD) activators),[4] mechanism-based inactivators (MBIs) of GABA-AT are attractive because of their unique inactivation mechanisms and their successful advancement into preclinical/clinical stages.[4] Unlike other irreversible inhibitors, MBIs are unreactive prior to conversion into an active species in the catalytic site of the target enzyme, thus minimizing unwanted off-target effects.[6]

Vigabatrin (1, Sabril®, FIG. 1B), a MBI of GABA-AT, exhibits anticonvulsant activity and was approved by the FDA in 2009 as an adjunctive therapy for refractory partial seizures.[7] Mechanistic studies revealed that it irreversibly inhibits GABA-AT by covalent modification through two different mechanisms, a Michael addition pathway (70%) and an enamine pathway (30%), leading to its anticonvulsant effect.[8, 9] It was also found to prevent cocaine addiction at a dose of 300 mg/kg in a rat model.[10] However, there are considerable concerns regarding the permanent visual damage associated with long-term vigabatrin administration, which results because of its low inactivation efficiency and poor blood-brain barrier (BBB) permeability, which demand high daily doses (1-3 g per day) that eventually impair its clinical profile.[11, 12] Recent findings identified cyclopentane-based analogue CPP-115 (2, FIG. 1B) and cyclopentene-based analogue OV329 (3, FIG. 1B), which exhibit several hundred-fold improved inactivation efficiency relative to vigabatrin.[13, 14] GABA-AT crystal structures in complex with CPP-115/OV329 demonstrated that their difluoromethylenyl groups are converted into a carboxylate group in the binding site, and both compounds inactivate the enzyme via tight electrostatic interactions between the two carboxylate groups and two arginine residues (Arg192 and Arg445).[14, 15] CPP-115 has been investigated in a Phase I clinical trial[10] and as a compassionate use medication[16] as a treatment for infantile spasms, while OV329 suppressed the release of brain dopamine at a dose of 0.1 mg/kg in a rat model of cocaine addiction.[14] Therefore, mechanism-based inactivation of GABA-AT has served as an effective approach to discover novel therapeutic treatments for different neurological disorders.

In 2000, (1R,3S,4S)-3-amino-4-fluorocyclopentane carboxylic acid (FCP, 4, FIG. 1B) was reported as an inactivator of GABA-AT.[17] In 2004, crystallography with GABA-AT revealed that FCP covalently modifies the Lys329-PLP linkage by forming imine adduct M5 (Scheme 1) derived from an enamine inactivation mechanism.[18] The proposed inactivation mechanism of FCP is initiated by FCP acting as a substrate to form Schiff base M1 with PLP, followed by deprotonation (M2) and subsequent elimination of fluoride ion to afford the imine intermediate (M3). Subsequent Lys329 attack at the imine moiety of M3 releases the enamine metabolite (M4) and PLP is returned to Lys329. M4 covalently modifies the Lys329-PLP complex to generate adduct M5 via an enamine mechanism. However, except for the co-crystal structure, its mechanism was not well supported. Therefore, at the beginning of this work, we resynthesized FCP (Scheme 2) and further elucidated its mechanisms of inactivation and alternative turnover using mass spectrometry with the intent of using this as a basis for new inactivator design.

Scheme 2. Synthetic route to FCP (4)[a].

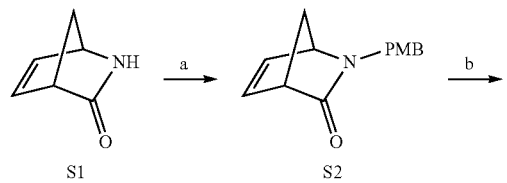

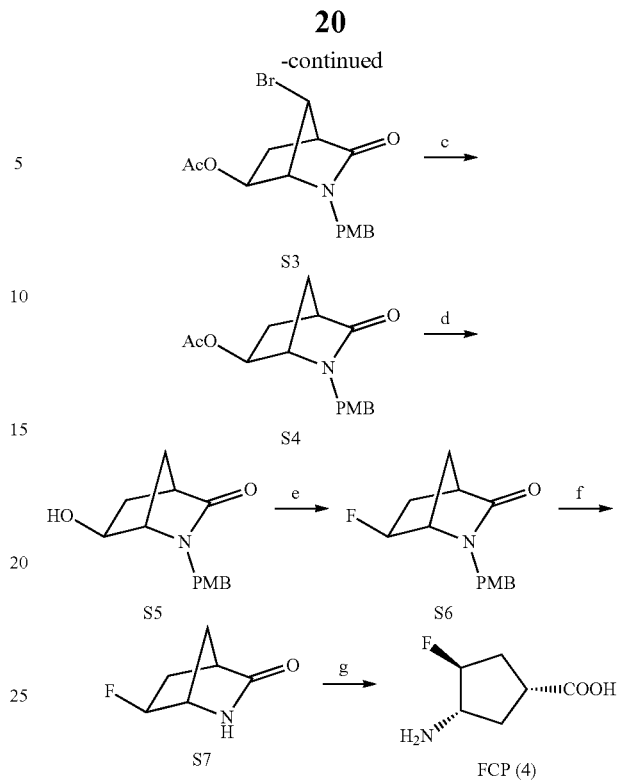

*Reagents and conditions:
(a) i) p-anisyl alcohol, conc. HCl, rt,
ii) NaH, TBAI, THF/DMF (10:1), 0° C.-rt;
(b) DBDMH, Ac₂O, rt;
(c) Bu₃SnH, benzene, reflux;
(d) K₂CO₃, MeOH/H₂O, rt;
(e) DAST, DCM, -78° C.-rt;
(f) ceric ammonium nitrate, CH₃CN/H₂O, 0° C.-rt;
(g) 4 N HCl, 70° C.

In the present work, the kinetic constants for FCP against GABA-AT (Table 1) indicate that FCP had a greater binding affinity ($K_I$=0.053 mM) toward GABA-AT but a lower maximum rate of inactivation ($k_{inact}$) against GABA-AT (0.011 min$^{-1}$) than vigabatrin, which eventually led to a modest inactivation efficiency, defined by the $k_{inact}/K_I$ ratio (0.20 min$^{-1}$ mM$^{-1}$).[19] It was reported that FCP exhibited a partition ratio of 147 with GABA-AT, meaning that 148 equivalents of FCP are turned over per active site for each equivalent of compound leading to inactivation.[17, 18] Moreover, 148 equivalents of fluoride ion are released per inactivation event, detected with a fluoride ion-selective electrode,[15] indicating that all turnovers require a fluoride ion elimination reaction.[17, 18] Tandem mass spectrometry in the present study of FCP with GABA-AT identified two main metabolites, whose masses fit enamine metabolite M4 or its imine tautomer M6 ([M+H]$^+$, theoretical: 128.0706; observed: 128.0705); subsequent hydrolysis gave ketone metabolite M7 ([M−1]$^−$, theoretical: 127.0401; observed: 127.0391), all with supporting MS$^2$ fragmentation (Scheme 1). According to the literature, FCP shows a different turnover mechanism when incubated with aspartate aminotransferase, affording a ketone metabolite without releasing fluoride ion (S11 in Scheme 3).[20] In the current study with GABA-AT we did not detect this metabolite. Intact protein mass spectrometry of GABA-AT inactivated by FCP produced a mass shift caused by covalent modification, which corresponded to PLP-bound ketone M8 (Scheme 1, theoretical: 357.06 Da; observed: 357.27 Da, shown in Table 2).

Ketone M8 is the product generated from imine adduct M5 via hydrolysis under liquid chromatography and mass spectrometry conditions, thereby validating the crystal structure. Therefore, high-resolution intact protein mass spectrometry is an important additional approach to facilitate protein adduct structure determination. The inactivation and alternative turnover mechanisms of FCP are summarized in Scheme 1. After deprotonation to M2, exclusive fluoride ion elimination affords M3, which is attacked by Lys329 at the iminium group, releasing enamine metabolite M4. Most of enamine M4 tautomerizes to the corresponding imine (M6), which undergoes hydrolysis to ketone M7, while only a very minor portion of M4 (0.7% of FCP according to its partition ratio) inactivates the enzyme by enamine addition to PLP, forming M5.

4-amino-5-fluoropentanoic acid (5, FIG. 1B), the open-chain analogue of FCP, improved potency against GABA-AT with a comparable rate constant.[21]

Figure 2:
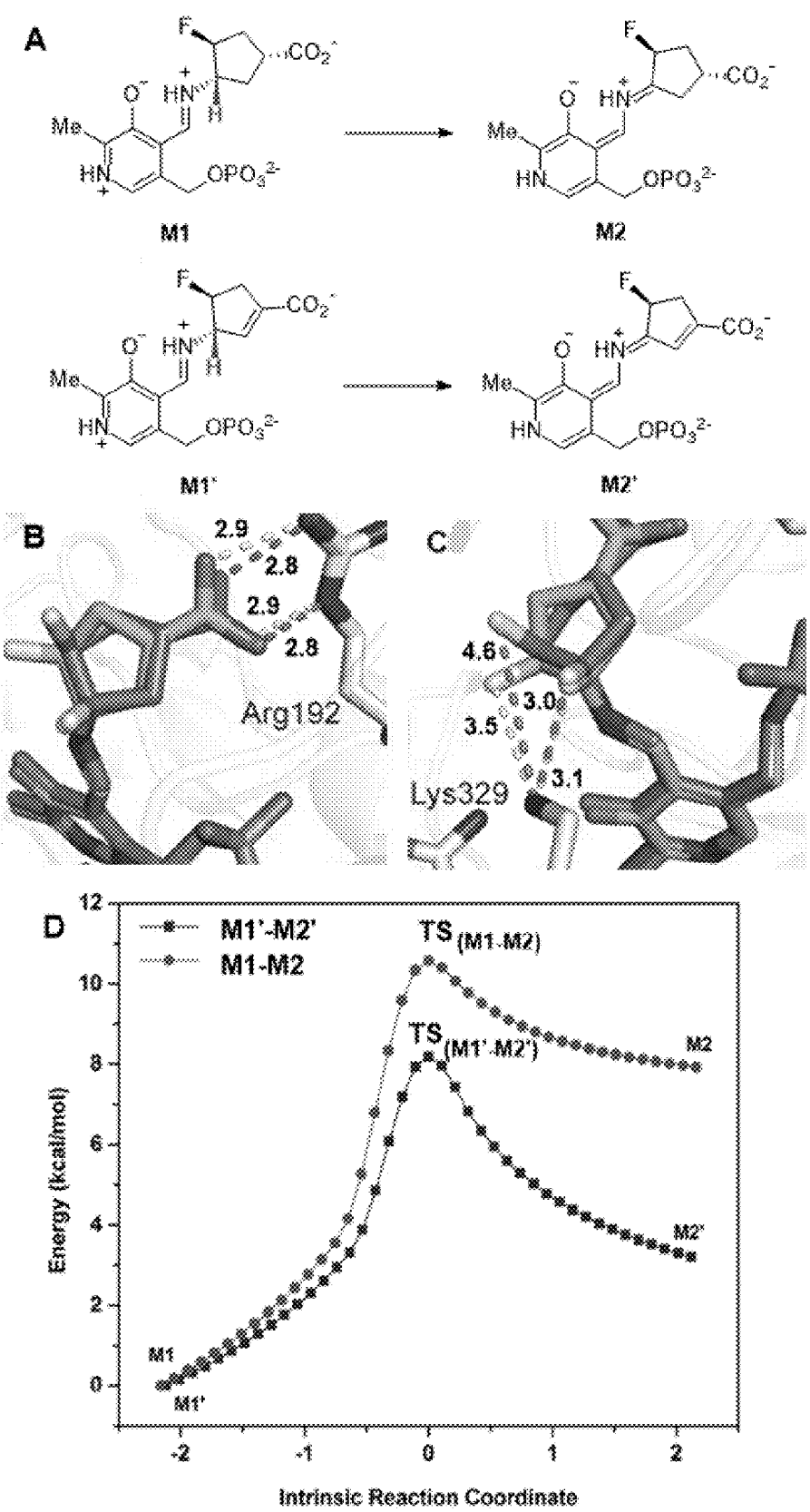
FIG. 2. Computational simulation results of PLP-bound ligands M1 and M1'. (A) The deprotonation reactions of PLP-bound ligand M1/M1' to M2/M2'. (B-C) Superimposed docking poses of M1 and M1' with GABA-AT. Ligands and selected residues in GABA-AT are shown in stick representation. (D) Reaction profile of the deprotonation reactions of M1 to M2 (circle) and M1' to M2' (square) in aqueous phase, calculating at a B3LYP/6-31+G(d,p) level of theory.

To explore the effect of the double bond on the scaffold of FCP, we initially conducted molecular docking studies to predict the binding poses of PLP-bound ligands in the binding site of GABA-AT and quantum mechanical cluster calculations to investigate the reaction profiles of the deprotonation steps.[22] The docking pose comparison of M1 and M1' (FIG. 2A) suggests that by incorporation of a double bond does not change the salt bridge interactions between Arg192 and the carboxylate group (FIG. 2B) and retains the PLP-bound ligand in a similar distance to Lys329, which abstracts the adjacent proton (FIG. 2A). It should be noted that the conformational change does bring the fluorine atom

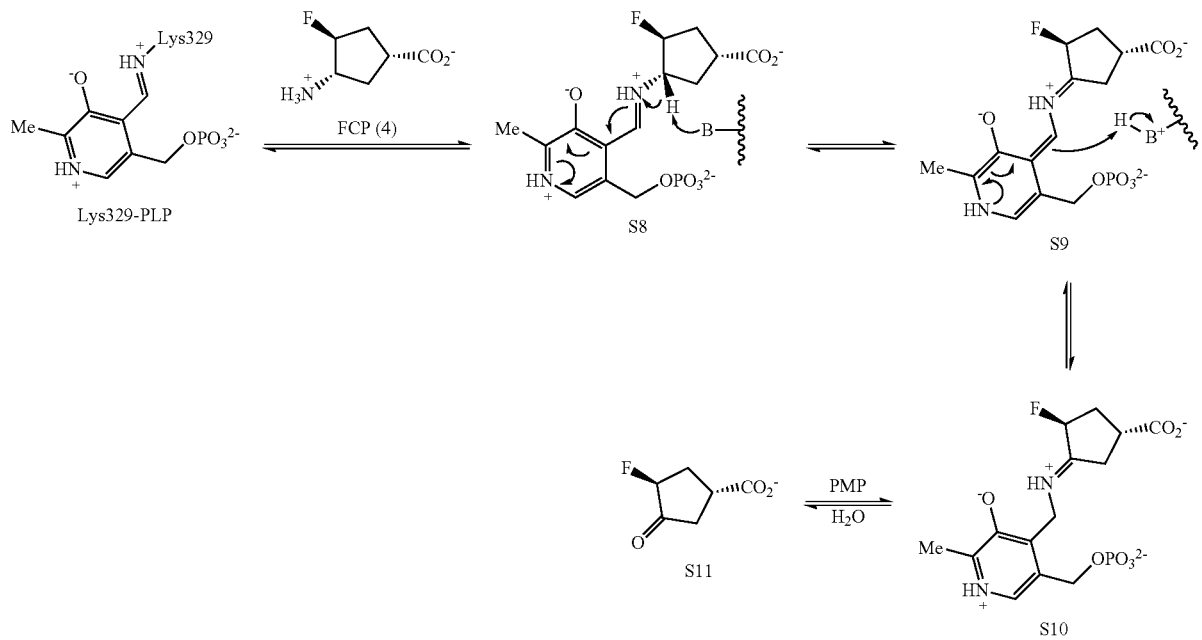

Scheme 3. Additional possible turnover pathway.

With the mechanisms of FCP clarified, we directed our attention to improving its inactivation efficiency. FCP exhibits good potency against GABA-AT ($K_I$=0.053 mM), similar to that of CPP-115 ($K_I$=0.059 mM),[14] a MBI that completed a successful Phase I clinical trial. However, the low maximal rate constant ($k_{inact}$=0.011 min$^{-1}$) of FCP with GABA-AT limits its inactivation efficiency. As illustrated in Scheme 1, there are three steps leading to inactivation: deprotonation (M1 to M2), fluoride elimination (M2 to M3), and enamine addition (M4 to M5). The deprotonation step was suggested as the rate-determining step rather than the cleavage of the carbon-fluorine bond in the original FCP article.[17] Our recent findings revealed that OV329 (FIG. 1B) was about ten times more efficient than CPP-115 as an inactivator of GABA-AT.[14] Computational simulations suggested that the incorporation of an endocyclic double bond into the scaffold of CPP-115 is able to bring the difluoromethylenyl group closer to the Lys329 residue, which is responsible for the enhanced binding affinity of OV329 ($K_I$=0.010 mM).[14] Furthermore, the added double bond led to a 1.5-fold enhancement of the $k_{inact}$ value. Additionally, it was also reported that the incorporation of a double bond into closer to Lys329 (from 4.6 Å to 3.5 Å) (FIG. 2C). Intriguingly, quantum mechanical cluster calculations of the deprotonation step catalyzed by Lys329 (FIG. 2D) demonstrate that the ligand-PLP Schiff base MV, containing the added double bond, displays about a 3 kcal/mol lower transition state (TS) energy in going to M2' compared with intermediate M1, generated from FCP, giving M2. This indicates that deprotonation of M1' is much easier than of M1. As deprotonation is considered the rate-determining step, we hypothesized that the lower TS energy from M1' to M2' should improve the overall inactivation rate, thereby enhancing the $k_{inact}$ value.

To assess the actual effect of this double bond, we synthesized and evaluated several cyclopentene analogues bearing different halogens. The synthetic route to prepare cyclopentene compound 6a bearing a fluorine atom (Scheme 4) was initiated with (1R)-(−)-2-azabicyclo[2.2.1]hept-5-en-3-one (7), which was protected with a p-methoxybenzyl (PMB) group (8), peroxidized with m-CPBA (9), followed by peroxide opening and selective acylation with BF$_3$·OEt$_2$ to afford the bicyclic key intermediate (10) containing a hydroxyl group on the bridgehead.

Methoxymethyl (MOM) protection (11), diacylation (12), and fluorination with DAST led to the corresponding fluorinated bicycle (13) as a single diastereomer. The full retention of relative configuration results from the formation of a transient aziridinium intermediate.[23] Subsequent MOM deprotection (14) and tosylation with PMB deprotection afforded lactam 15, containing the tosylate group on the bridgehead to act as a leaving group in the next step. Introduction of a tert-butyloxycarbonyl (Boc) protecting group on the lactam nitrogen of 15, followed by a one-pot hydrolysis of the lactam and elimination of the tosylate with $K_2CO_3$/MeOH afforded the desired cyclopentene key intermediate (16). Removal of the Boc group and methyl ester under acidic conditions afforded the final product (6a) as a HCl salt, whose structure was confirmed by $^1H$, $^{13}C$, and 2D NMR spectrometries.

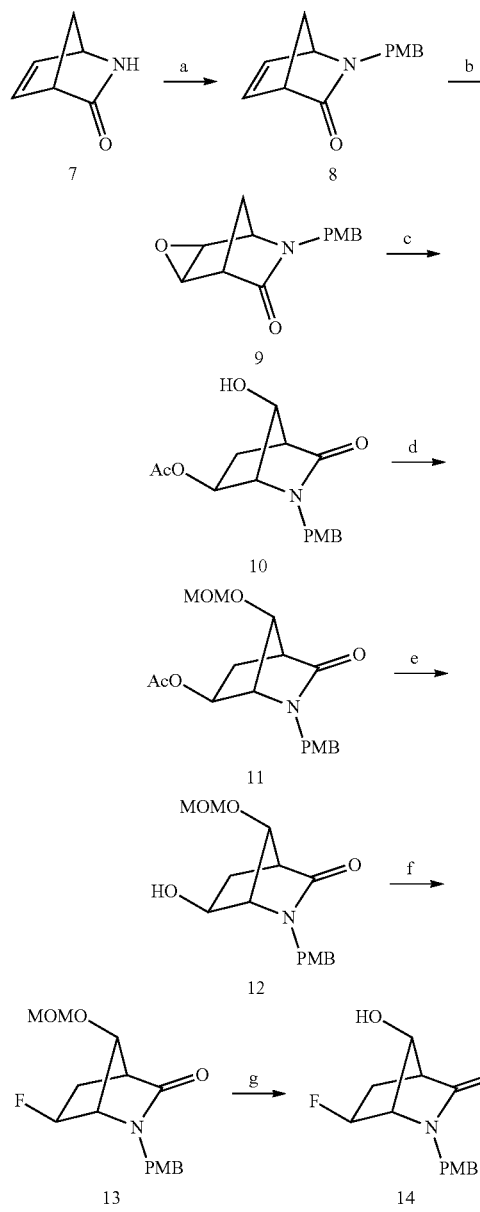

Scheme 4. Synthetic Route to 6a[a]

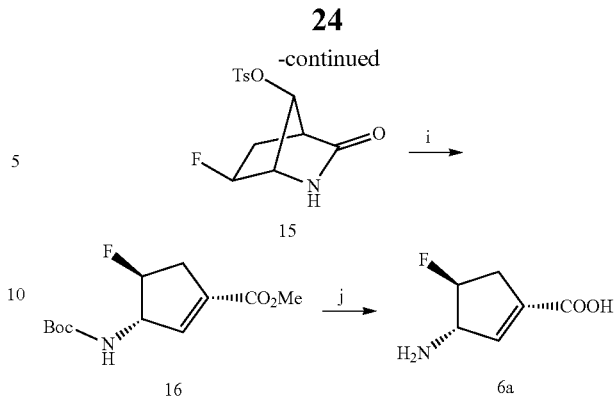

*Reagents and conditions:
(a) i) p-anisyl alcohol, conc. HCl, rt;
ii) NaH, TBAI, THF/DMF (10:1), 0° C.-rt;
(b) m-CPBA, CHCl₃, reflux;
(c) BF₃·OEt₂, AcOH, DCM, rt;
(d) MOMCl, DIPEA, DCM, rt;
(e) K₂CO₃, MeOH/H₂O, rt;
(f) DAST, DCM, -78° C.-rt;
(g) 6 N HCl, THF, 80° C.;
(h) i) TsCl, DIPEA, DMAP, CH₃CN, rt;
ii) ceric ammonium nitrate, CH₃CN/H₂O, rt;
(i) i) Boc₂O, DIPEA, DMAP, DCM, rt;
ii) K₂CO₃, MeOH, rt;
(j) 4N HCl, AcOH, 70° C.

To prepare two other cyclopentene analogues (6b and 6c), bearing chlorine and bromine atoms, respectively, the synthetic routes were initiated from tosylation (17) and PMB deprotection of 10 to afford 18 (Scheme 5). After Boc protection (19), a one-pot hydrolysis and elimination was carried out with $K_2CO_3$/MeOH to obtain the desired cyclopentene (20). Intermediate 20 was successfully converted to the desired monochloro-(21a) or monobromo- (21b) substituted compound using NCS or NBS, respectively; the sole diastereomers formed may have been facilitated by neighboring group participation in the halogenation step.[17, 24] Final cyclopentene products 6b and 6c were obtained as HCl salts after deprotection.

Scheme 5. Synthetic Route to 6b and 6b[a]

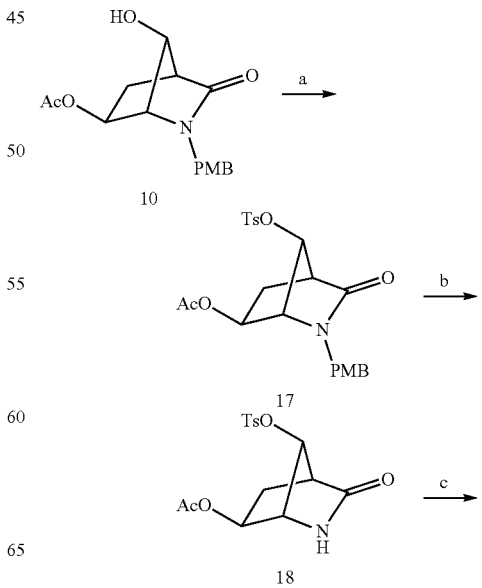

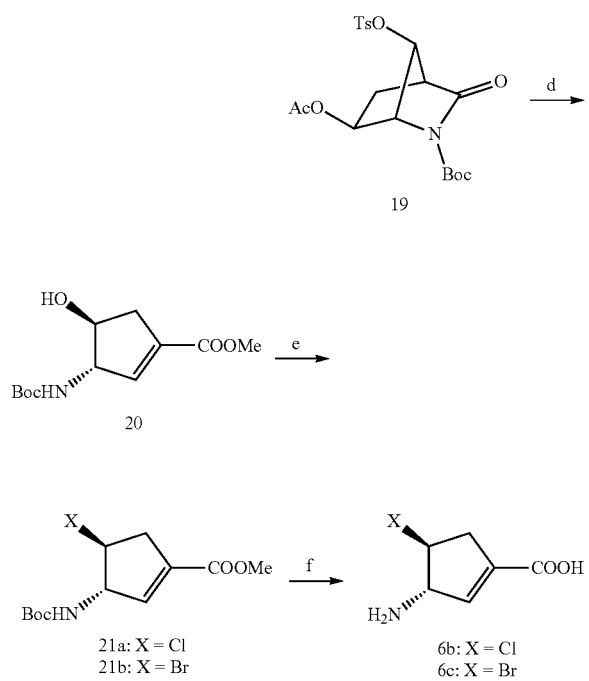

*Reagents and conditions:
(a) TsCl, DIPEA, DMAP, CH$_3$CN, rt;
(b) ceric ammonium nitrate, CH$_3$CN/H$_2$O, rt;
(c) Boc$_2$O, DIPEA, DCM, rt;
(d) K$_2$CO$_3$, MeOH, rt;
(e) NBS or NCS, Ph$_3$P, DMF, rt;
(f) 4N HCl, AcOH, 70° C.

The kinetic constants shown in Table 1 indicate that: (a) Compared to FCP, new cyclopentene analogues 6a-c exhibited about a 10-fold enhancement of their rate constants with GABA-AT. (b) Chloro- (6b) and bromo-substituted (6c) analogues showed much lower binding affinities to GABA-AT, corresponding to the larger sizes of the halogens, while the fluoro-substituted analogue (6a) showed a 2-fold enhancement of binding affinity compared to FCP, thereby establishing that 6a is about 25-times more efficient than FCP as an inactivator of GABA-AT. The correspondence of the inactivation rate constants for 6a-c supports the notion that the rate-determining step is deprotonation rather than carbon-halogen bond cleavage.

TABLE 1

Kinetic Constants of Analogues FCP and 6a-c with GABA-AT[a]

| Compound | $k_{inact}$ (min$^{-1}$) | $K_I$ (mM) | $k_{inact}/K_I$ (min$^{-1}$mM$^{-1}$) |
|---|---|---|---|
| FCP (4) | 0.011 ± 0.001 | 0.053 ± 0.022 | 0.21 |
| 6a | 0.132 ± 0.023 | 0.026 ± 0.011 | 5.08 |
| 6b | 0.135 ± 0.010 | 6.01 ± 0.89 | 0.022 |
| 6c | 0.086 ± 0.011 | 14.26 ± 3.94 | 0.006 |
| vigabatrin (1) | 0.21 ± 0.03 | 0.29 ± 0.09 | 0.727 |

[a]Data were collected from a time-dependent assay in duplicate according to the experimental protocols in ref 14. $k_{inact}$ and $K_I$ values were determined by the equation: $k_{obs} = k_{inact}*[I]/(K_I + [I])$ and are presented as means with standard errors.

Figure 4:
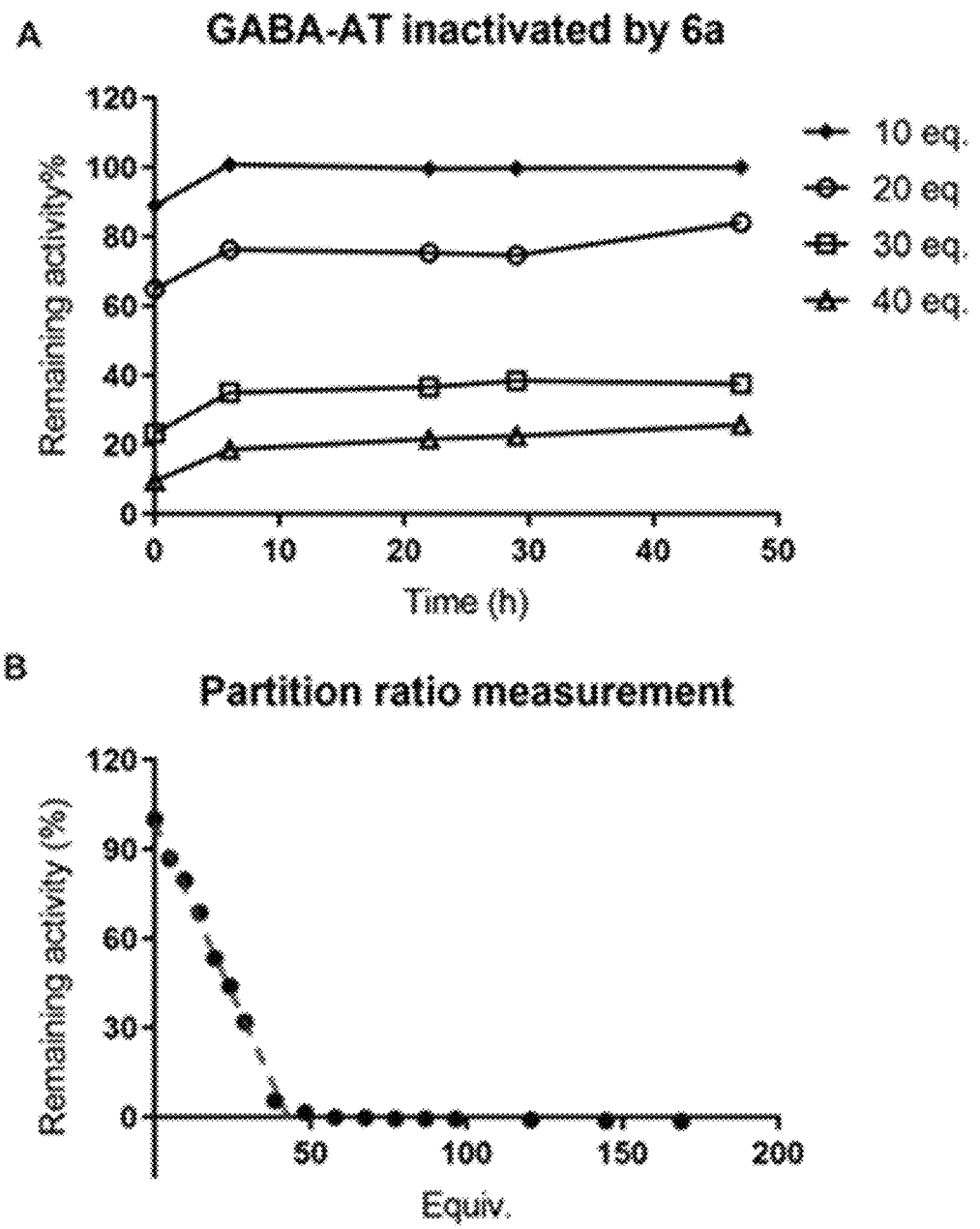
FIG. 4. Dialysis and partition ratio determination of 6a with GABA-AT. (A) Dialysis of GABA-AT inactivated by 10-40 equivalents of 6a overnight at 25° C. (B) Remaining activity of the GABA-AT inactivated by 0-170 equivalents of 6a overnight at 25° C.

The irreversibility of the inhibition of GABA-AT by 6a was assessed by dialysis. After four days of dialysis against buffer containing excess PLP and α-KG there was no regeneration of enzyme activity, confirming that 6a is an inactivator of GABA-AT (FIG. 4A). Consequently, we investigated the potential adduct structures generated from 6a-c using intact protein mass spectrometry. The results shown in Table 2 demonstrate that 6a-c, bearing different halogens, resulted in identical molecular mass shifts after inactivation of GABA-AT, which match the ketone-PLP adduct structure (M6' in Scheme 6, calculated: 355.05 Da; found: 355.02-355.42 Da) generated from an enamine addition pathway. Hydrolysis of the imine in M5' to M6' might have occurred during chromatography and mass spectrometry. This suggests that they all covalently bind to GABA-AT through the same mechanism as FCP (Scheme 1) after forming M3' via halide ion elimination (Scheme 6).

TABLE 2

Intact Protein Mass Results of 6a-c and FCP with GABA-AT[a]

| Compound | Structure | Native peak (Da) | Modified peak (Da) | Adduct (Da)[b] |
|---|---|---|---|---|
| FCP (4) | F, H$_2$N-cyclopentane-COOH | 53080.26 ± 0.93 | 53437.54 ± 0.60 | 357.27 |
| 6a | F, H$_2$N-cyclopentene-COOH | 53080.51 ± 0.63 | 53435.93 ± 0.88 | 355.42 |
| 6b | Cl, H$_2$N-cyclopentene-COOH | 53079.54 ± 0.67 | 53434.56 ± 0.77 | 355.02 |
| 6c | Br, H$_2$N-cyclopentene-COOH | 53079.87 ± 0.74 | 53435.28 ± 0.87 | 355.41 |

[a]Data are presented as deconvoluted masses (in Daltons) with associated standard deviations around average protein masses.
[b]Mass shifts were obtained by subtracting average native masses (no PLP attached) from average modified masses.

Scheme 6. Inactivation and Turnover Mechanism of GABA-AT by 6a.

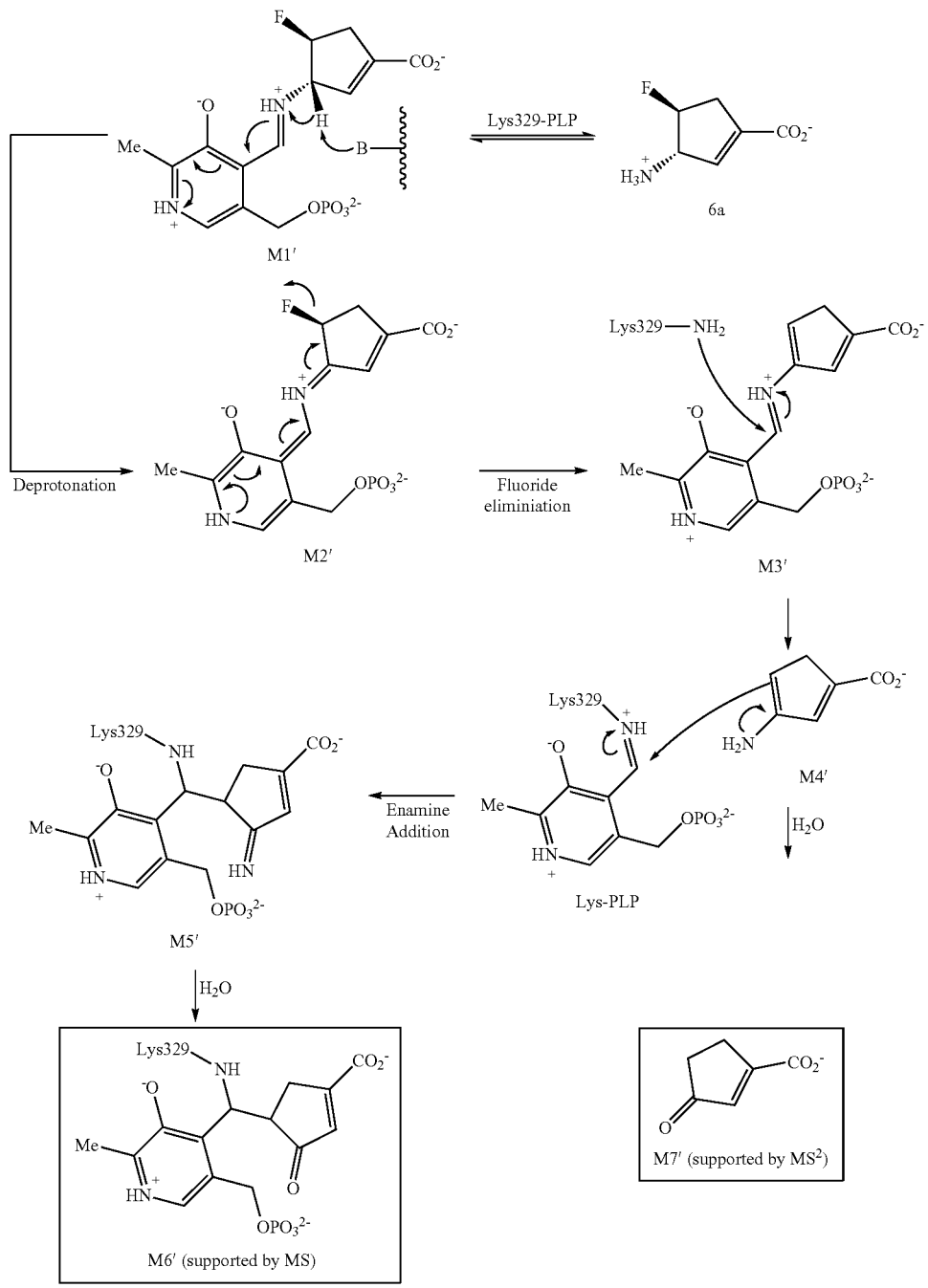

Figure 3:
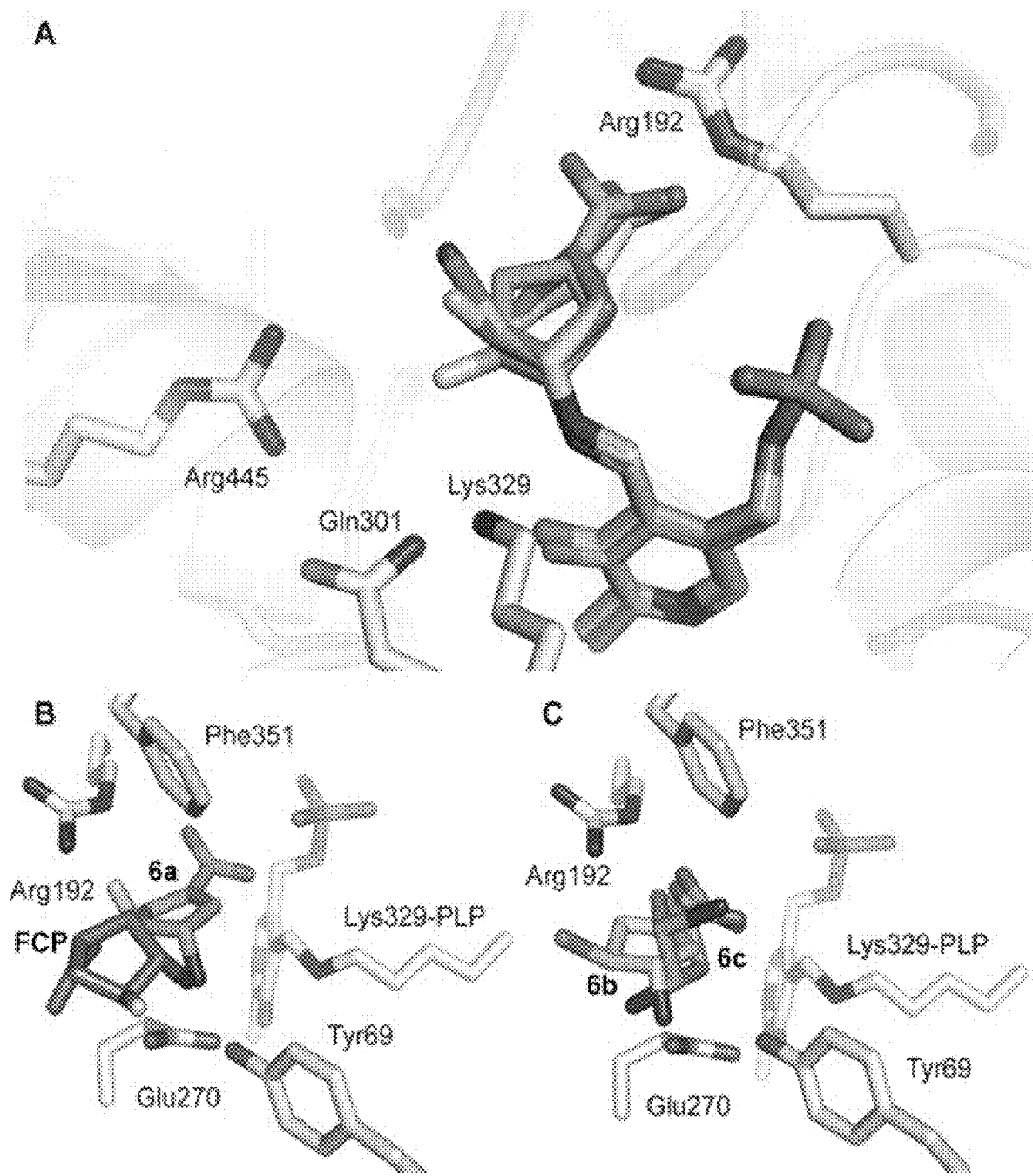
FIG. 3. Superimposed docking poses of FCP, 6a, 6b, and 6c in Schiff bases with PLP from GABA-AT (A). Docking study results for FCP and 6a prior to reaction with Lys329-PLP (B). Docking study results for 6b and 6c prior to reaction with Lys329-PLP (C). Ligands and selected residues in GABA-AT are shown in stick representation.

Superimposed docking poses in FIG. 3A of 6a-c exhibit similar binding poses as FCP after forming PLP-bound intermediates, such as M1'. Docking studies of FCP and 6a-c in the binding site of GABA-AT show that the amino groups of FCP and 6a display similar orientations toward the Lys329-PLP linkage (FIG. 3B), which is beneficial for the reaction with the PLP ligand in the initial binding step, while the amino groups of 6b and 6c orient away from the Lys329-bound PLP (FIG. 3C). These modeling results suggest that the initial binding step with Lys329-PLP may play the most significant role in influencing their binding affinity, leading to the distinct $K_I$ values.

The partition ratio for 6a was determined to be 44, and 44 equivalents of fluoride ions were release per inactivation event (FIG. 4B), indicating that 97.8% of 6a underwent fluoride ion elimination per inactivation event. Tandem mass spectra of 6a with GABA-AT identified ketone M7' (Scheme 6) ([M–H]⁻, calculated: 125.0244; found: 125.0234), generated by fluoride ion elimination and enamine hydrolysis, as the major metabolite with its confirmatory MS² fragmentation pattern. No ketone metabolite containing a fluorine atom was detected, confirming that enamine hydrolysis is the sole alternative turnover pathway for 6a.

The inactivation and turnover mechanism for 6a are proposed in Scheme 6. After capturing the PLP ligand from Lys329, PLP-bound M1' undergoes deprotonation and fluoride ion elimination to form the imine intermediate (M3'). According to the enamine pathway, Lys329 attacks the imine moiety of M3', which leads to the release of enamine metabolite M4', mostly hydrolyzing to M7'. A small amount of M4' (2.2% of 6a according to its partition ratio) attaches to the Lys329-PLP linkage, forming M5', and inactivates the enzyme in a manner similar to that by FCP. Compared to original inactivator FCP, incorporation of the extra double bond decreases the partition ratio (147 for FCP[18] vs 44 for 6a) and leads to a 2-fold greater binding affinity with reduced transition state energy for the rate-determining deprotonation step, which is responsible for a 12-fold enhancement in the rate constant, making 6a 25-fold more efficient as an inactivator of GABA-AT than FCP.

We also assessed the selectivity of 6a over other ATs, including ornithine aminotransferase (Orn-AT), aspartate aminotransferase (Asp-AT), and alanine aminotransferase (Ala-AT). 6a showed no inhibitory effect on Asp-AT or Ala-AT up to a concentration of 10 mM.[14] In a time-dependent assay against Orn-AT,[25] 6 a displayed a comparable rate constant ($k_{inact}$=0.143±0.014 min$^{-1}$) but 10-fold weaker binding affinity ($K_I$=0.25±0.06 mM) relative to its effect with GABA-AT.

In summary, GABA-AT is a druggable target for neurological disorders based on the demonstration that mechanism-based inactivation is an effective approach to irreversibly inhibit the activity of this essential enzyme in neurotransmitter metabolism. In this work, we established a GABA-AT MBI discovery strategy using computational simulation, organic synthesis, mechanistic enzymology, and intact protein- and small molecule mass spectrometry. These approaches allowed us to better understand inactivation and alternative turnover mechanisms of a known inactivator, FCP. Furthermore, this strategy facilitated the design of new MBIs, leading to the identification of compound 6a as a more efficient inactivator of GABA-AT than FCP.

REFERENCES FOR EXAMPLE 1

1. Jansonius, J. N., Structure, evolution and action of vitamin B6-dependent enzymes. *Curr. Opin. Struct. Biol.* 1998, 8, 759-769.
2. Hwang, B. Y.; Cho, B. K.; Yun, H.; Koteshwar, K.; Kim, B. G., Revisit of aminotransferase in the genomic era and its application to biocatalysis. *J. Mol. Catal. B-Enzym.* 2005, 37, 47-55.
3. Lee, H.; Juncosa, J. I.; Silverman, R. B., Ornithine aminotransferase versus GABA aminotransferase: implications for the design of new anticancer drugs. *Med. Res. Rev.* 2015, 35, 286-305.
4. Silverman, R. B., Design and mechanism of GABA aminotransferase inactivators. treatments for epilepsies and addictions. *Chem. Rev.* 2018, 118, 4037-4070.
5. Yogeeswari, P.; Sriram, D.; Vaigundaragavendran, J., The GABA shunt: an attractive and potential therapeutic target in the treatment of epileptic disorders. *Curr. Drug Metab.* 2005, 6, 127-139.
6. Silverman, R. B., The potential use of mechanism-based enzyme inactivators in medicine. *J. Enzyme Inhib.* 1988, 2, 73-90.
7. Krauss, G.; Faught, E.; Foroozan, R.; Pellock, J. M.; Sergott, R. C.; Shields, W. D.; Ziemann, A.; Dribinsky, Y.; Lee, D.; Toni, S.; Othman, F.; Isojarvi, J., Sabril® registry 5-year results: Characteristics of adult patients treated with vigabatrin. *Epilepsy Behav.* 2016, 56, 15-19.
8. Meldrum, B. S.; Murugaiah, K., Anticonvulsant action in mice with sound-induced seizures of the optical isomers of gamma-vinyl GABA. *Eur. J. Pharmacol.* 1983, 89, 149-152.
9. Nanavati, S. M.; Silverman, R. B., Mechanisms of inactivation of gamma-aminobutyric-acid aminotransferase by the antiepilepsy drug gamma-vinyl gaba (vigabatrin). *J. Am. Chem. Soc.* 1991, 113, 9341-9349.
10. Silverman, R. B., The 2011 E. B. Hershberg award for important discoveries in medicinally active substances: (1S,3S)-3-amino-4-difluoromethylenyl-1-cyclopentanoic acid (CPP-115), a GABA aminotransferase inactivator and new treatment for drug addiction and infantile spasms. *J. Med. Chem.* 2012, 55, 567-575.
11. Wild, J. M.; Smith, P. E. M.; Knupp, C., Objective derivation of the morphology and staging of visual field loss associated with long-term vigabatrin therapy. *CNS Drugs* 2019, 33, 817-829.
12. Walters, D. C.; Arning, E.; Bottiglieri, T.; Jansen, E. E. W.; Salomons, G. S.; Brown, M. N.; Schmidt, M. A.; Ainslie, G. R.; Roullet, J. B.; Gibson, K. M., Metabolomic analyses of vigabatrin (VGB)-treated mice: GABA-transaminase inhibition significantly alters amino acid profiles in murine neural and non-neural tissues. *Neurochem. Int* 2019, 125, 151-162.
13. Pan, Y.; Gerasimov, M. R.; Kvist, T.; Wellendorph, P.; Madsen, K. K.; Pera, E.; Lee, H.; Schousboe, A.; Chebib, M.; Brauner-Osborne, H.; Craft, C. M.; Brodie, J. D.; Schiffer, W. K.; Dewey, S. L.; Miller, S. R.; Silverman, R. B., (1S, 3S)-3-Amino-4-difluoromethylenyl-1-cyclopentanoic acid (CPP-115), a potent gamma-aminobutyric acid aminotransferase inactivator for the treatment of cocaine addiction. *J. Med. Chem.* 2012, 55, 357-366.
14. Juncosa, J. I.; Takaya, K.; Le, H. V.; Moschitto, M. J.; Weerawarna, P. M.; Mascarenhas, R.; Liu, D.; Dewey, S. L.; Silverman, R. B., Design and mechanism of (S)-3-amino-4-(difluoromethylenyl)cyclopent-1-ene-1-carboxylic acid, a highly 1. Jansonius, J. N., Structure, evolution and action of vitamin B6-dependent enzymes. *Curr. Opin. Struct. Biol.* 1998, 8, 759-769.
15. Lee, H.; Doud, E. H.; Wu, R.; Sanishvili, R.; Juncosa, J. I.; Liu, D.; Kelleher, N. L.; Silverman, R. B., Mechanism of inactivation of gamma-aminobutyric acid aminotransferase by (1S,3S)-3-amino-4-difluoromethylene-1-cyclopentanoic acid (CPP-115). *J. Am. Chem. Soc.* 2015, 137, 2628-2640.
16. Doumlele, K.; Conway, E.; Hedlund, J.; Tolete, P.; Devinsky, O., A case report on the efficacy of vigabatrin analogue (1S, 3S)-3-amino-4-difluoromethylenyl-1-cyclopentanoic acid (CPP-115) in a patient with infantile spasms. *Epilepsy Behav. Case Rep.* 2016, 6, 67-69.
17. Qiu, J.; Silverman, R. B., A new class of conformationally rigid analogues of 4-amino-5-halopentanoic acids, potent inactivators of gamma-aminobutyric acid aminotransferase. *J. Med. Chem.* 2000, 43, 706-720.
18. Storici, P.; Qiu, J.; Schirmer, T.; Silverman, R. B., Mechanistic crystallography. Mechanism of inactivation of gamma-aminobutyric acid aminotransferase by (1R, 3S,4S)-3-amino-4-fluorocyclopentane-1-carboxylic acid as elucidated by crystallography. *Biochemistry* 2004, 43, 14057-14063.
19. Strelow, J. M., A perspective on the kinetics of covalent and irreversible inhibition. *SLAS Discov.* 2017, 22, 3-20.
20. Mascarenhas, R.; Le, H. V.; Clevenger, K. D.; Lehrer, H. J.; Ringe, D.; Kelleher, N. L.; Silverman, R. B.; Liu, D., Selective targeting by a mechanism-based inactivator against pyridoxal 5'-phosphate-dependent enzymes: Mechanisms of inactivation and alternative turnover. *Biochemistry* 2017, 56, 4951-4961.

21. Bey, P.; Gerhart, F.; Jung, M., Synthesis of (E)-4-amino-2,5-hexadienoic acid and (E)-4-amino-5-fluoro-2-pentenoic acid—irreversible inhibitors of 4-aminobutyrate-2-oxoglutarate aminotransferase. *J. Org. Chem.* 1986, 51, 2835-2838.

22. Maeda, S.; Harabuchi, Y.; Ono, Y.; Taketsugu, T.; Morokuma, K., Intrinsic reaction coordinate: Calculation, bifurcation, and automated search. *Int. J. Quantum Chem.* 2015, 115, 258-269.

23. Bournaud, C.; Bonin, M.; Micouin, L., Skeletal rearrangements in the 2,3-diazanorbornene series. A fast access to highly functionalized cyclopentanes. *Org. Lett.* 2006, 8, 3041-3043.

24. Katagiri, N.; Matsuhashi, Y.; Kokufuda, H.; Takebayashi, M.; Kaneko, C., A highly efficient synthesis of the antiviral agent (+)-cyclaradine involving the regioselective cleavage of epoxide by neighboring participation. *Tetrahedron Lett.* 1997, 38, 1961-1964.

25. Juncosa, J. I.; Lee, H.; Silverman, R. B., Two continuous coupled assays for ornithine-delta-aminotransferase. *Anal. Biochem.* 2013, 440, 145-149.

26. Wang, Zhiyong; Silverman, Richard B. Synthesis and evaluation of fluorinated conformationally restricted analogues of GABA as potential inhibitors of GABA aminotransferase. *Bioorganic & Medicinal Chemistry* (2006), 14(7), 2242-2252.

27. Silverman, Richard B.; Ilan, Yaron. Ornithine aminotransferase inhibition with GABA analogues for treatment of hepatocellular carcinoma. PCT Int. App. (2016), WO 2016/073983 A2 20160512.

28. Silveraman, Richard B.; Le, Hoang V.; McLeod, Rima L.; Hawker, Dustin D. Inactivators of *Toxoplasma gondii* ornithine aminotransferase for treating toxoplasmosis and malaria. U.S. Pat. Appl. Publ. (2018), US20180098952 A1 20180412.

Example 2

Reference is made to the Supporting Information of the article Shen and Silverman, "Mechanism-Based Design of 3-Amino-4-Halocyclopentenecarboxylic Acids as Inactivators of GABA Aminotransferase", *ACS Med. Chem. Lett.* 2020, 11, 10, 1949-1955, the content of which his incorporated by reference in entirety.

The following example provides supporting information for the information disclosed in Example 1 as follows.

General Procedure. Commercially available reagents and solvents were used without further purification. All reactions were monitored by thin-layer chromatography (TLC) using 0.25 mm SiliCycle extra hard 250 μM TLC plates (60 F254), and spots were visualized under UV (254 nm) and ceric ammonium molybdate or ninhydrin stain. Flash chromatography was performed on a Combi-Flash Rf system (Teledyne ISCO) with silica columns and reversed-phase C-18 columns. Analytical HPLC was used to determine the purity of all of the final products using an Agilent 1260 series instrument with the following conditions: column, Phenomenex Kintex C-18 column (50×2.1 mm, 2.6 μm); mobile phase, 5-100% acetonitrile/water containing 0.05% TFA at a flow rate of 0.9 mL/min for 6 min; UV detection at 254 nm. The purity of all tested compounds for in vitro biological studies was >95% by HPLC analysis. $^1$H, $^{13}$C, and 2D NMR spectra were obtained using Bruker AVANCE III 500 MHz system and Bruker NEO console w/QCI-F cryoprobe 600 MHz system. Chemical shifts were reported relative to CDCl$_3$ (δ=7.26 for $^1$H NMR and δ=77.16 for $^{13}$C NMR spectra), CD$_3$OD (δ=3.31 for $^1$H NMR and δ=49.15 for $^{13}$C NMR spectra), and DMSO-d$_6$ (δ=2.50 for $^1$H NMR and δ=39.52 for $^{13}$C NMR spectra). The following abbreviations for multiplicities were used: s=singlet, d=doublet, t=triplet, q=quartet, m=multiplet, dd=doublet of doublets, dt=doublet of triplets, dq=doublet of quartets, ddt=doublet of doublet of triplets, ddd=doublet of doublet of doublets, dddd=doublet of doublet of doublet of doublets, dddt=doublet of doublet of doublet of triplets, and br s=broad singlet. Low-resolution mass spectra (LRMS) were obtained using a Thermo TSQ Quantum system in the positive ion mode using atmospheric pressure chemical ionization (APCI) with a reversed-phase Agilent Infinity 1260 HPLC system. High resolution mass spectra (HRMS) were obtained on an Agilent 6210 LC-TOF spectrometer in the positive ion mode using electrospray ionization (ESI) with an Agilent G1312A HPLC pump and an Agilent G1367B autoinjector at the Integrated Molecular Structure Education and Research Center (IMSERC), Northwestern University.

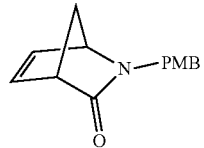

S2

(1R,4S)-2-(4-Methoxybenzyl)-2-azabicyclo[2.2.1]hept-5-en-3-one (S2).$^2$ (i) p-Anisyl alcohol (10 mL) and conc. HCl (15 mL) were dissolved in a 100 mL round-bottom three necked flask at room temperature. The resulting mixture was stirred at room temperature for an additional 1 h. After the completion of the reaction, the solution was poured into ice and extracted with EtOAc (20 mL×3). The combined organic layers were separated, washed with sat. Na$_2$CO$_3$ solution and brine, dried over Na$_2$SO$_4$, and concentrated under vacuum. Fresh 4-methoxybenzyl chloride was obtained as a colorless oil (9.2 g, 52%) and was used directly in the next step without further purification. (ii) To a stirred solution of (1R,4S)-2-azabicyclo[2.2.1]hept-5-en-3-one (S1, CAS number: 79200-56-9, 5.8 g, 53 mmol) in dry THF (300 mL) was added NaH (60%, 3.18 g, 80 mmol) suspended in DMF (30 mL) in an ice bath. The resulting mixture was stirred at the same temperature for 30 min, followed by the addition of 4-methoxybenzyl chloride (9.2 g, 63.6 mmol) and TBAI (1.96 g, 5.3 mmol) at 0° C. The resulting mixture was slowly warmed to room temperature and stirred for an additional 3 h. After the completion of the reaction, the solution was quenched with water (200 mL) and extracted with EtOAc (100 mL×3). The combined organic layers were separated, washed with sat. Na$_2$CO$_3$ solution and brine, dried over Na$_2$SO$_4$, and concentrated under vacuum. The crude product was purified via Combi-Flash chromatography (EtOAc-hexane: 0-50%) to yield S2 (7.8 g, 65%) as a colorless oil. $^1$H NMR (500 MHz, CD$_3$OD) δ 7.12 (d, J=8.5 Hz, 2H), 6.87 (d, J=8.6 Hz, 2H), 6.62-6.50 (m, 2H), 4.24 (d, J=14.6 Hz, 1H), 4.16 (q, J=1.9 Hz, 1H), 4.10 (d, J=14.6 Hz, 1H), 3.77 (s, 3H), 3.32-3.30 (m, 1H), 2.25 (dt, J=7.7, 1.8 Hz, 1H), 2.07 (dt, J=7.7, 1.6 Hz, 1H). $^{13}$C NMR (126 MHz, CD$_3$OD) δ 182.5, 160.8, 141.6, 137.6, 130.9 (2C), 129.2, 115.0 (2C), 64.6, 60.0, 55.9, 55.1, 47.8. LRMS. T$_R$=2.28 min; [M+H]$^+$: 230.1.

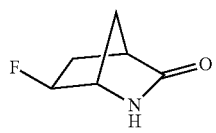

S7

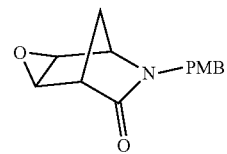

9

(1S,4R,6S)-6-Fluoro-2-azabicyclo[2.2.1]heptan-3-one (S7). i) To a stirred solution of 5S (460 mg, 1.86 mmol, prepared following the published procedures[2] from S2) in DCM (10 mL) was added DAST (0.51 mL, 2.80 mmol) at −78° C. The resulting mixture was slowly warmed to room temperature and stirred overnight. After the completion of the reaction, the solution was quenched with water and extracted with EtOAc (30 mL×3). The combined organic layers were separated, washed with brine, dried over $Na_2SO_4$, and concentrated under vacuum. The crude product was purified via Combi-Flash chromatography (EtOAc-hexane: 0-100%) to yield S6 as a colorless oil. LRMS. $T_R$=2.35 min; [M+H]$^+$: 250.13. ii) To a stirred solution of S6 in $CH_3CN$ (10 mL) was added an aqueous solution of ceric ammonium nitrate (3.00 g in 3 mL water, 5.58 mmol) at room temperature. The resulting mixture was stirred for 2 h until the starting material completely disappeared. The residue was extracted with EtOAc (25 mL×3). The combined organic layers were separated, washed with sat. $Na_2CO_3$ solution and brine, dried over $Na_2SO_4$, and concentrated under vacuum. The crude product was purified via Combi-Flash chromatography (EtOAc-hexane: 0-100%) to yield S7 (40 mg, 17% over two steps) as a white powder. $^1$H NMR (500 MHz, CDCl$_3$) δ 5.69 (br s, 1H), 4.89 (ddq, J=54.1, 6.4, 1.5 Hz, 1H), 3.93 (d, J=2.3 Hz, 1H), 2.68 (q, J=2.1 Hz, 1H), 2.23-2.04 (m, 2H), 1.97-1.76 (m, 2H). $^{13}$C NMR (126 MHz, CDCl$_3$) δ 180.6, 92.1 (d, J=192.0 Hz), 57.4 (d, J=27.2 Hz), 42.5, 37.9 (d, J=2.0 Hz), 33.0 (d, J=20.9 Hz). LRMS. $T_R$=0.32 min; [M+H]$^+$: 129.81.

(1S,2R,4S,5R)-6-(4-Methoxybenzyl)-3-oxa-6-azatricyclo[3.2.1.0]octan-7-one[2, 4] (9). To a stirred solution of 8 or S2 (7.8 g, 34.5 mmol) in CHCl$_3$ (150 mL) was added m-CPBA (15.4 g, 70 mmol) at room temperature. The resulting mixture was heated to reflux overnight under an argon atmosphere. After the completion of the reaction, the solution was quenched with sat. $NaS_2O_3$ solution and extracted with CHCl$_3$ (100 mL×3). The combined organic layers were separated, washed with sat. $Na_2CO_3$ solution and brine, dried over $Na_2SO_4$, and concentrated under vacuum. The crude product was purified via Combi-Flash chromatography (EtOAc-hexane: 0-100%) to yield 9 (3.9 g, 46%) as a yellow oil. $^1$H NMR (500 MHz, CDCl$_3$) δ 7.18 (d, J=8.6 Hz, 2H), 6.86 (d, J=8.6 Hz, 2H), 4.44 (d, J=14.6 Hz, 1H), 4.23 (d, J=14.6 Hz, 1H), 3.80 (s, 3H), 3.76 (d, J=1.6 Hz, 1H), 3.53 (dd, J=3.7, 1.6 Hz, 1H), 3.23 (dd, J=3.7, 1.3 Hz, 1H), 2.99 (q, J=1.5 Hz, 1H), 1.79 (d, J=9.5 Hz, 1H), 1.58 (dt, J=9.6, 1.9 Hz, 1H). $^{13}$C NMR (126 MHz, CDCl$_3$) δ 176.9, 159.3, 129.6 (2C), 129.4, 114.2 (2C), 59.5, 55.4, 55.3, 51.8, 47.3, 45.5, 30.3. LRMS. $T_R$=2.08 min; [M+H]$^+$: 246.12.

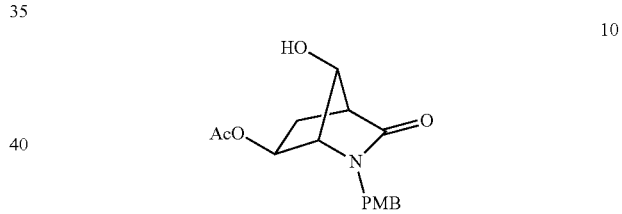

10

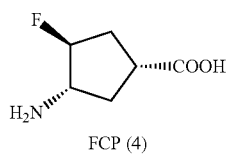

FCP (4)

(1R,3S,4S)-3-Amino-4-fluorocyclopentanecarboxylic acid hydrochloric acid salt (4, FCP). S7 (40 mg, 0.31 mmol) was dissolved in 4N HCl (4 mL) at room temperature. The resulting mixture was heated at 70° C. for 1 h. After the completion of the reaction, the excess solvent was removed under vacuum. The crude product was purified via Combi-Flash chromatography (C18 Reverse Column, CH$_3$CN/H$_2$O: 0-100%) to yield FCP (1) as a white powder HCl salt (50 mg, 88%). $^1$H NMR (500 MHz, CD$_3$OD) δ 5.10 (ddt, J=52.3, 6.6, 3.9 Hz, 1H), 3.88-3.67 (m, 1H), 3.23-3.07 (m, 1H), 2.54 (dt, J=13.4, 7.9 Hz, 1H), 2.40-2.18 (m, 2H), 1.86 (dt, J=13.6, 9.2 Hz, 1H). $^{13}$C NMR (126 MHz, CD$_3$OD) δ 177.2, 96.81 (d, J=181.0 Hz), 57.84 (d, J=27.7 Hz), 41.1 (d, J=1.4 Hz), 35.51 (d, J=22.6 Hz), 33.05 (d, J=3.1 Hz). HRMS (ESI) calcd for C$_6$H$_{11}$FNO$_2$ [M+H]$^+$: 148.0768; found, 148.0766.

(1S,4S,6S,7R)-7-Hydroxy-2-(4-methoxybenzyl)-3-oxo-2-azabicyclo[2.2.1]heptan-6-yl acetate (10). To a stirred solution of 9 (3.9 g, 15.9 mmol) in AcOH/DCM (15 mL/80 mL) was added BF$_3$·OEt$_2$ (3.12 mL, 23.9 mmol) at 0° C. under an argon atmosphere. The resulting mixture was slowly warmed to room temperature and stirred for an additional 2 h. After the completion of the reaction, the reaction was quenched with water and extracted with EtOAc (50 mL×3). The combined organic layers were separated, washed with sat. Na$_2$CO$_3$ solution and brine, dried over Na$_2$SO$_4$, and concentrated under vacuum. The crude product was purified via Combi-Flash chromatography (methanol-DCM: 0-10%) to yield 10 (3.5 g, 72%) as an off-white solid. $^1$H NMR (500 MHz, CDCl$_3$) δ 7.19 (d, J=8.6 Hz, 2H), 6.87 (d, J=8.5 Hz, 2H), 4.82 (dd, J=7.7, 3.0 Hz, 1H), 4.62 (d, J=14.6 Hz, 1H), 4.10 (s, 1H), 3.97 (d, J=14.6 Hz, 1H), 3.80 (s, 3H), 3.58 (d, J=1.9 Hz, 1H), 2.81 (dt, J=3.9, 1.9 Hz, 1H), 2.29 (dd, J=13.8, 7.7 Hz, 1H), 2.09 (dt, J=13.8, 3.8 Hz, 1H), 2.05 (s, 3H). $^{13}$C NMR (126 MHz, CDCl$_3$) δ 173.9, 170.0, 159.3, 129.7 (2C), 128.2, 114.3 (2C), 76.9, 73.1, 62.0, 55.3, 49.7, 44.0, 29.7, 21.0. LRMS. $T_R$=1.89 min; [M+H]$^+$: 306.51.

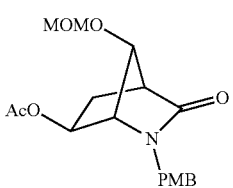

11

(1R,4S,6S,7R)-2-(4-Methoxybenzyl)-7-(methoxymethoxy)-3-oxo-2-azabicyclo-[2.2.1]heptan-6-yl acetate (11). To a stirred solution of 10 (1.3 g, 4.26 mmol) in dry DCM (60 mL) was added DIPEA (3.25 mL, 14.76 mmol) and MOMCl (1.3 mL, 17.0 mmol) at 0° C. under argon. The resulting mixture was slowly warmed to room temperature and stirred overnight. After the completion of the reaction, the solution was quenched with water and extracted with DCM (30 mL×3). The combined organic layers were separated, washed with sat. $Na_2CO_3$ solution and brine, dried over $Na_2SO_4$, and concentrated under vacuum. The crude product was purified via Combi-Flash chromatography (EtOAc-hexane: 0-100%) to yield 11 (1.45 g, 98%) as a colorless oil. $^1$H NMR (500 MHz, $CDCl_3$) δ 7.19 (d, J=8.4 Hz, 2H), 6.87 (d, J=8.4 Hz, 2H), 4.71 (dd, J=7.9, 3.7 Hz, 1H), 4.62 (d, J=14.7 Hz, 1H), 4.59 (d, J=6.6 Hz, 1H), 4.56 (d, J=6.6 Hz, 1H), 3.98 (d, J=14.7, 1H), 3.97 (s, 1H), 3.80 (s, 3H), 3.70 (d, J=2.0 Hz, 1H), 3.34 (s, 3H), 2.83 (dt, J=3.9, 1.8 Hz, 1H), 2.24 (dd, J=13.2, 7.7 Hz, 1H), 2.17-2.09 (m, 1H), 2.02 (s, 3H). $^{13}$C NMR (126 MHz, $CDCl_3$) δ 173.8, 170.7, 159.3, 129.7 (2C), 128.3, 114.2 (2C), 95.4, 80.2, 72.8, 61.3, 55.9, 55.3, 48.4, 44.0, 30.0, 21.1, 21.0. LRMS. $T_R$=2.29 min; [M+H]$^+$: 350.61.

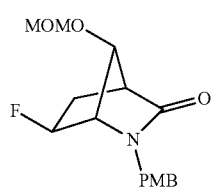

13

(1S,4S,6S,7R)-6-Fluoro-2-(4-methoxybenzyl)-7-(methoxymethoxy)-2-azabicyclo-[2.2.1]heptan-3-one (13). To a stirred solution of 12 (920 mg, 3.0 mmol) in DCM (50 mL) was added DAST (0.6 mL, 4.5 mmol) at −78° C. The resulting mixture was slowly warmed to room temperature and stirred overnight. After the completion of the reaction, the solution was quenched with water and extracted with EtOAc (30 mL×3). The combined organic layers were separated, washed with brine, dried over $Na_2SO_4$, and concentrated under vacuum. The crude product was purified via Combi-Flash chromatography (EtOAc-hexane: 0-100%) to yield 13 (700 mg, 75.3%) as colorless oil. $^1$H NMR (500 MHz, $CDCl_3$) δ 7.15 (d, J=8.5 Hz, 2H), 6.87 (d, J=8.7 Hz, 2H), 4.61 (d, J=4.6 Hz, 2H), 4.54 (dddt, J=53.7, 7.2, 2.6, 1.2 Hz, 1H), 4.36 (d, J=14.7 Hz, 1H), 4.17 (d, J=14.7 Hz, 1H), 4.03 (s, 1H), 3.80 (s, 3H), 3.78 (s, 1H), 3.35 (s, 3H), 2.83 (s, 1H), 2.31-2.13 (m, 2H). $^{13}$C NMR (126 MHz, $CDCl_3$) δ 173.6, 159.4, 129.5 (2C), 128.2, 114.3 (2C), 95.8, 90.8 (d, J=197.3 Hz), 80.6, 61.9 (d, J=24.1 Hz), 55.9, 55.2, 48.1 (d, J=2.5 Hz), 44.2, 30.7 (d, J=21.8 Hz). LRMS. $T_R$=2.34 min; [M+H]$^+$: 310.51.

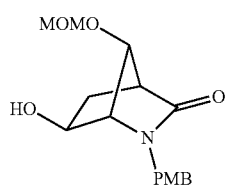

12

(1R,4S,6S,7R)-6-Hydroxy-2-(4-methoxybenzyl)-7-(methoxymethoxy)-2-azabi-cyclo[2.2.1]heptan-3-one (12). To a stirred solution of 11 (1.45 g, 4.17 mmol) in MeOH/$H_2O$ (40/8 mL) was added $K_2CO_3$ (2.3 g, 16.7 mmol) at room temperature. The resulting mixture was stirred at room temperature for 3 h. After the completion of the reaction, the solution was neutralized with sat. $NH_4Cl$ solution and extracted with EtOAc (50 mL×3). The combined organic layers were separated, washed with brine, dried over $Na_2SO_4$, and concentrated under vacuum. The crude product was purified via Combi-Flash chromatography (EtOAc-hexane: 0-100%) to yield 12 as a colorless oil (1.23 g, 84%) $^1$H NMR (500 MHz, $CDCl_3$) δ 7.16 (d, J=8.6 Hz, 2H), 6.86 (d, J=8.7 Hz, 2H), 4.68-4.59 (m, 2H), 4.46 (d, J=14.6 Hz, 1H), 4.14-4.03 (m, 2H), 3.91-3.82 (m, 1H), 3.80 (d, J=1.3 Hz, 3H), 3.52 (d, J=2.0 Hz, 1H), 3.37 (d, J=1.3 Hz, 3H), 2.88 (dt, J=3.8, 1.8 Hz, 1H), 2.26 (dd, J=13.6, 7.4 Hz, 1H), 1.86 (dt, J=13.5, 3.5 Hz, 1H). $^{13}$C NMR (126 MHz, $CDCl_3$) δ 173.7, 159.3, 129.5 (2C), 128.5, 114.2 (2C), 95.9, 81.8, 62.9, 56.2, 55.3, 48.3, 44.0, 33.7. LRMS. $T_R$=1.85 min; [M+H]$^+$: 308.44.

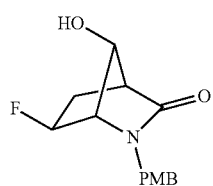

14

(1S,4S,6S,7R)-6-Fluoro-7-hydroxy-2-(4-methoxybenzyl)-2-azabicyclo[2.2.1]-heptan-3-one (14). To a stirred solution of 13 (700 mg, 2.26 mmol) in THF (10 mL) was added 6 N HCl (20 mL) at room temperature, and the resulting mixture was heated at 85° C. for 1 h. After the completion of the reaction, the solution was neutralized with a sat. $Na_2CO_3$ solution and extracted with EtOAc (25 mL×3). The combined organic layers were separated, washed with sat. $Na_2CO_3$ solution and brine, dried over $Na_2SO_4$, and concentrated under vacuum. The crude product was purified via Combi-Flash chromatography (EtOAc-hexane: 0-100%) to yield 14 (400 mg, 66%) as a colorless oil. $^1$H NMR (500 MHz, $CD_3OD$) δ 7.21 (d, J=8.7 Hz, 2H), 6.92 (d, J=8.6 Hz, 2H), 4.61 (dddt, J=53.7, 7.2, 2.6, 1.2 Hz, 1H), 4.39 (d, J=14.6 Hz, 1H), 4.18 (d, J=14.7 Hz, 1H), 4.09 (s, 1H), 3.79 (s, 3H), 3.71 (s, 1H), 2.65 (dq, J=3.0, 1.6 Hz, 1H), 2.26 (ddt, J=29.1, 13.4, 3.4 Hz, 1H), 2.10 (td, J=12.8, 7.1 Hz, 1H). $^{13}$C NMR (126 MHz, $CD_3OD$) δ 176.8, 161.0, 130.7 (2C), 129.8, 115.3 (2C), 92.2 (d, J=194.7 Hz), 77.3, 64.6 (d, J=23.8 Hz), 55.7, 50.8 (d, J=2.6 Hz), 45.0, 31.1 (d, J=21.8 Hz). LRMS. $T_R$=1.89 min; [M+H]$^+$: 266.24.

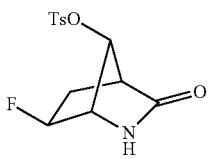

(1S,4S,6S,7R)-6-Fluoro-3-oxo-2-azabicyclo[2.2.1]heptan-7-yl 4-methylbenzene-sul-fonate (15). (i) To a stirred solution of 14 (400 mg, 1.50 mmol) in CH$_3$CN (20 mL) were added DIPEA (0.53 mL, 3.0 mmol), DMAP (366 mg, 3.0 mmol), and TsCl (433 mg, 2.25 mmol) at room temperature, and the resulting mixture was stirred at room temperature overnight. After the completion of the reaction, the solution was quenched with water and extracted with EtOAc (25 mL×3). The combined organic layers were separated, washed with sat. Na$_2$CO$_3$ solution and brine, dried over Na$_2$SO$_4$, and concentrated under vacuum. The crude product was purified via Combi-Flash chromatography (EtOAc-hexane: 0-100%) to yield the lactam intermediate (470 mg, 75%) as a colorless oil. LRMS. T$_R$=2.95 min; [M+H]$^+$: 420.54. (ii) To a stirred solution of the lactam intermediate (470 mg, 1.12 mmol) in CH$_3$CN (30 mL) was added an aqueous solution of ceric ammonium nitrate (1.84 g in 10 mL water) at room temperature. The resulting mixture was stirred for 2 h until the starting material disappeared. After the completion of the reaction, the solution was extracted with EtOAc (25 mL×3). The combined organic layers were separated, washed with sat. Na$_2$CO$_3$ solution and brine, dried over Na$_2$SO$_4$, and concentrated under vacuum. The crude product was purified via Combi-Flash chromatography (EtOAc-hexane: 0-100%) to yield 15 (230 mg, 69%) as a white solid. $^1$H NMR (500 MHz, CDCl$_3$) δ 7.81 (d, J=8.3 Hz, 2H), 7.37 (d, J=8.1 Hz, 2H), 6.15 (s, 1H), 4.91-4.76 (m, 1H), 4.75 (q, J=1.8 Hz, 1H), 4.05-3.92 (m, 1H), 2.81-2.72 (m, 1H), 2.47 (s, 3H), 2.27-2.16 (m, 2H). $^{13}$C NMR (126 MHz, CDCl$_3$) δ 174.0, 145.6, 132.8, 130.0 (2C), 128.0 (2C), 91.1 (d, J=197.6 Hz), 80.1, 58.4 (d, J=24.9 Hz), 46.7 (d, J=2.3 Hz), 29.2 (d, J=22.3 Hz), 21.7. LRMS. T$_R$=2.22 min; [M+F1]$^+$: 300.12.

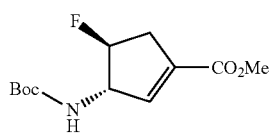

(3S,4S)-Methyl 3-((tert-butoxycarbonyl)amino)-4-fluorocyclopent-1-enecarboxy-late (16). (i) To a stirred solution of 15 (230 mg, 0.77 mmol) in DCM (10 mL) were added DIPEA (0.15 mL, 0.85 mmol), DMAP (10 mg, 0.077 mmol), and Boc$_2$O (194 mg, 0.85 mmol) at room temperature, and the resulting mixture was stirred at room temperature overnight. After the completion of the reaction, the solution was quenched with sat. NH$_4$Cl solution and extracted with DCM (25 mL×3). The combined organic layers were separated, washed with brine, dried over Na$_2$SO$_4$, and concentrated under vacuum. The crude product was obtained as a light brown oil (300 mg, 98%) and was used in next step without further purification. (ii) To a stirred solution of the intermediate (300 mg, 0.75 mmol) in MeOH (10 mL) was added K$_2$CO$_3$ (311 mg, 2.25 mmol) at room temperature. Then the resulting mixture was stirred for an additional 1 h and then neutralized with sat. NH$_4$Cl solution and extracted with EtOAc (25 mL×3). The combined organic layers were separated, washed with brine, dried over Na$_2$SO$_4$, and concentrated under vacuum. The crude product was purified via Combi-Flash chromatography (EtOAc-Hexane: 0-100%) to yield 16 (160 mg, 82%) as a white solid. $^1$H NMR (500 MHz, CDCl$_3$) δ 6.58 (s, 1H), 5.08 (ddt, J=51.5, 6.0, 2.7 Hz, 1H), 4.80 (d, J=21.7 Hz, 1H), 4.72-4.53 (m, 1H), 3.76 (s, 3H), 3.14-2.99 (m, 1H), 2.82-2.69 (m, 1H), 1.44 (s, 9H). $^{13}$C NMR (126 MHz, CDCl$_3$) δ 164.4, 154.8, 138.7, 136.2, 97.4 (d, J=183.5 Hz), 80.3, 62.7 (d, J=30.1 Hz), 51.9, 37.3 (d, J=24.7 Hz), 28.3 (3C). LRMS. T$_R$=2.57 min; [M−Boc+H]$^+$: 158.91.

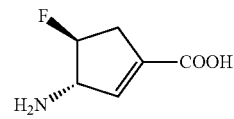

(3S,4S)-3-Amino-4-fluorocyclopent-1-enecarboxylic acid hydrochloric acid salt (6a). To a stirred solution of 16 (160 mg, 0.62 mmol) in acetic acid (6 mL) was added 4N HCl (6 mL) at room temperature, and the resulting mixture was heated at 70° C. overnight. After the completion of the reaction, the excess solvent was removed under vacuum. The crude product was purified via Combi-Flash chromatography (C18 Reverse Phase Column, CH$_3$CN/H$_2$O: 0-100%) to afford 6a as a white powder HCl salt (90 mg, 81%). $^1$H NMR (500 MHz, CD$_3$OD) δ 6.58 (s, 1H), 5.36 (ddt, J=50.9, 6.4, 2.9 Hz, 1H), 4.56 (dt, J=22.6, 2.3 Hz, 1H), 3.30-3.14 (m, 1H), 2.85 (dddd, J=27.8, 18.4, 3.1, 1.4 Hz, 1H). $^{13}$C NMR (126 MHz, CD$_3$OD) δ 166.1, 142.0, 134.1 (d, J=2.5 Hz), 96.0 (d, J=182.3 Hz), 63.3 (d, J=31.2 Hz), 38.7 (d, J=24.3 Hz). HRMS (ESI) calcd for C$_6$H$_9$FNO$_2$ [M+H]$^+$: 146.0612; found, 146.0613.

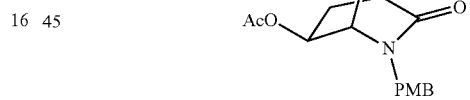

(1R,4S,6S,7R)-2-(4-Methoxybenzyl)-3-oxo-7-(tosyloxy)-2-azabicyclo[2.2.1]heptan-6-yl acetate (17). To a stirred solution of 10 (3.50 g, 11.48 mmol) in CH$_3$CN (150 mL) were added DIPEA (4.0 mL, 23 mmol), DMAP (2.8 g, 23 mmol), and TsCl (3.27 g, 17.2 mmol) at room temperature. The resulting mixture was stirred at room temperature overnight. After the completion of the reaction, the solution was quenched with water and extracted with EtOAc (100 mL×3). The combined organic layers were separated, washed with sat. Na$_2$CO$_3$ solution and brine, dried over Na$_2$SO$_4$, and concentrated under vacuum. The crude product was purified via Combi-Flash chromatography (EtOAc-hexane: 0-100%) to yield 17 (5.0 g, 95%) as a colorless oil. $^1$H NMR (500 MHz, CDCl$_3$) δ 7.68 (d, J=8.4 Hz, 2H), 7.31 (d, J=8.1 Hz, 2H), 7.17 (d, J=8.6 Hz, 2H), 6.88 (d, J=8.6 Hz, 2H), 4.69 (dd, J=7.8, 3.5 Hz, 1H), 4.53 (d, J=14.6 Hz, 1H), 4.37 (s, 1H), 4.01 (d, J=14.6 Hz, 1H), 3.89 (d, J=1.9 Hz, 1H), 3.83 (s, 3H), 2.76 (dt, J=4.0, 2.0 Hz, 1H), 2.46 (s, 3H), 2.22

(dd, J=13.6, 7.8 Hz, 1H), 2.10 (dt, J=13.5, 3.9 Hz, 1H), 2.05 (d, J=3.7 Hz, 3H). $^{13}$C NMR (126 MHz, CDCl$_3$) δ 171.4, 170.8, 159.4, 145.5, 132.6, 130.0 (2C), 129.8 (2C), 127.8 (2C), 127.7, 114.3 (2C), 79.7, 72.0, 61.4, 55.3, 47.6, 44.2, 29.4, 21.7, 21.0. LC-MS. T$_R$=2.89 min; [M+H]$^+$: 460.15.

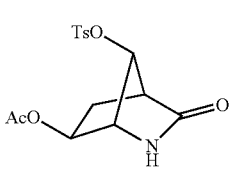

18

(1R,4S,6S,7R)-3-Oxo-7-(tosyloxy)-2-azabicyclo[2.2.1]heptan-6-yl acetate (18). To a stirred solution of 17 (5.0 g, 10.9 mmol) in CH$_3$CN (150 mL) was added an aqueous solution of ceric ammonium nitrate (17.9 g in 45 mL water, 32.7 mmol) at room temperature. The resulting mixture was stirred for 2 h until the starting material completely disappeared. The residue was extracted with EtOAc (100 mL×3). The combined organic layers were separated, washed with sat. Na$_2$CO$_3$ solution and brine, dried over Na$_2$SO$_4$, and concentrated under vacuum. The crude product was purified via Combi-Flash chromatography (EtOAc-hexane: 0-100%) to yield 18 (3.0 g, 81%) as a white solid. $^1$HNMR (500 MHz, CDCl$_3$) δ 7.80 (d, J=8.3 Hz, 2H), 7.38 (d, J=8.0 Hz, 2H), 5.74 (s, 1H), 4.96-4.79 (m, 1H), 4.54 (s, 1H), 4.16 (d, J=1.6 Hz, 1H), 2.72 (dd, J=3.8, 1.8 Hz, 1H), 2.47 (s, 3H), 2.25 (dd, J=13.7, 7.6 Hz, 1H), 2.16 (dt, J=13.7, 3.8 Hz, 1H), 2.10 (s, 3H). $^{13}$C NMR (126 MHz, CDCl$_3$) δ 173.4, 171.0, 145.7, 132.6, 130.2 (2C), 127.9 (2C), 80.2, 73.5, 58.4, 46.9, 28.4, 21.7, 21.0. LC-MS. T$_R$=2.30 min; [M+H]$^+$: 340.51.

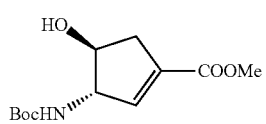

20

(3S,4S)-methyl 3-((tert-Butoxycarbonyl)amino)-4-hydroxycyclopent-1-enecarboxylate (20). (i) To a stirred solution of 18 (3.0 g, 8.85 mmol) in DCM (150 mL) were added DIPEA (1.69 mL, 9.70 mmol), DMAP (122 mg, 1.0 mmol), and Boc$_2$O (2.12 g, 9.70 mmol) at room temperature. The resulting mixture was stirred at room temperature overnight. After the completion of the reaction, the solution was quenched with sat. NH$_4$Cl solution and extracted with DCM (100 mL×3). The combined organic layers were separated, washed with brine, dried over Na$_2$SO$_4$, and concentrated under vacuum. The crude product (19) was obtained as a light brown oil (4.7 g) and was used in the next step without further purification. LC-MS. T$_R$=3.01 min; [M−t−Bu+H]$^+$: 383.61. (ii) To a stirred solution of the intermediate (~4.7 g) in MeOH (200 mL) was added K$_2$CO$_3$ (3.67 mg, 26.55 mmol) at room temperature. The resulting mixture was stirred for an additional 1 h and then neutralized with sat. NH$_4$Cl solution and extracted with DCM (100 mL×3). The combined organic layers were separated, washed with brine, dried over Na$_2$SO$_4$, and concentrated under vacuum. The crude product was purified via Combi-Flash chromatography (EtOAc-hexane: 0-100%) to yield 20 (1.4 g, 79% over two steps) as a white solid. $^1$H NMR (500 MHz, CDCl$_3$) δ 6.44 (s, 1H), 4.87 (s, 1H), 4.56 (d, J=2.6 Hz, 1H), 4.33 (ddd, J=7.8, 6.3, 5.0 Hz, 1H), 3.75 (s, 3H), 3.06-2.93 (m, 1H), 2.55 (ddd, J=16.8, 4.3, 2.4 Hz, 1H), 1.45 (s, 9H). $^{13}$C NMR (126 MHz, CDCl$_3$) δ 164.6, 156.7, 138.0, 136.7, 80.6, 65.7, 51.8, 38.3, 28.3 (3C). LC-MS. T$_R$=1.90 min; [M−t−Bu+H]$^+$: 201.53.

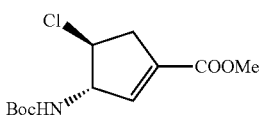

21a (3S,4S)-Methyl 3-((tert-Butoxycarbonyl)amino)-4-chlorocyclopent-1-enecarboxylate (21a) To a stirred solution of 20 (250 mg, 0.97 mmol) in DMF (20 mL) were added NCS (263 mg, 1.94 mmol) and Ph$_3$P (388 mg, 1.48 mmol) at room temperature. The resulting mixture was stirred for 2 h until the starting material completely disappeared. The residue was extracted with EtOAc (20 mL×3). The combined organic layers were separated, washed with water and brine, dried over Na$_2$SO$_4$, and concentrated under vacuum. The crude product was purified via Combi-Flash chromatography (EtOAc-hexane: 0-100%) to yield 21a (60 mg, 23%) as a white solid. $^1$H NMR (500 MHz, CDCl$_3$) δ 6.55 (d, J=2.2 Hz, 1H), 5.12 (d, J=9.6 Hz, 1H), 5.07 (t, J=7.3 Hz, 1H), 4.75 (t, J=5.6 Hz, 1H), 3.76 (s, 3H), 3.13-3.01 (m, 1H), 2.97 (dd, J=17.7, 1.4 Hz, 1H), 1.46 (s, 9H). $^{13}$C NMR (126 MHz, CDCl$_3$) δ 164.4, 155.1, 140.9, 134.8, 80.3, 62.7, 59.4, 51.9, 41.0, 28.3 (3C). LC-MS. T$_R$=2.68 min; [M+H−Boc]$^+$: 174.98.

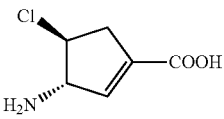

6b (3S,4S)-3-Amino-4-chlorocyclopent-1-enecarboxylic acid hydrochloric acid salt (6b) was synthesized following the same procedure for the synthesis of 6a, starting from 21a (60 mg, 0.22 mmol). The crude product was washed with acetonitrile to yield 6b as a white powder HCl salt (40 mg, 90%). $^1$H NMR (500 MHz, CD$_3$OD) δ 6.60 (q, J=2.1 Hz, 1H), 4.94 (td, J=6.4, 3.6 Hz, 1H), 4.64 (dd, J=6.2, 2.0 Hz, 1H), 3.27 (ddt, J=17.7, 6.8, 1.8 Hz, 1H), 2.98 (ddt, J=17.7, 3.4, 1.5 Hz, 1H). $^{13}$C NMR (126 MHz, CD$_3$OD) δ 166.2, 141.8, 135.1, 59.4, 59.0, 42.2. HRMS (ESI) calcd for C$_6$H$_9$ClNO$_2$ [M+H]$^+$: 162.0316; found, 162.0316.

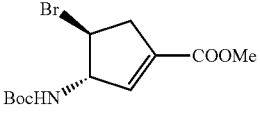

21b (3S,4S)-Methyl 4-Bromo-3-((tert-butoxycarbonyl)amino)cyclopent-1-enecarboxylate (21b) was synthesized following the same procedure for the synthesis of 21a, starting from 20 (200 mg, 0.78 mmol). The crude product was purified via Combi-Flash chromatography (EtOAc-hexane: 0-100%) to yield 21b (80 mg, 32%) as a white solid. $^1$H NMR (500 MHz, DMSO-d$_6$) δ 7.47 (d, J=7.7 Hz, 1H), 6.53

(s, 1H), 4.91 (td, J=5.9, 2.9 Hz, 1H), 4.69 (t, J=6.0 Hz, 1H), 3.70 (s, 3H), 3.15 (ddt, J=17.5, 6.4, 1.7 Hz, 1H), 2.87 (dd, J=17.4, 2.5 Hz, 1H), 1.40 (s, 9H). $^{13}$C NMR (126 MHz, DMSO-$d_6$) δ 163.9, 154.9, 140.9, 134.3, 78.3, 59.2, 56.5, 51.7, 40.9, 28.2 (3C). LC-MS. $T_R$=2.73 min; [M+H-Boc]$^+$: 218.97.

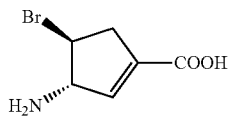

6c (3S,4S)-3-Amino-4-bromocyclopent-1-enecarboxylic acid hydrochloric acid salt (6c) was synthesized following the same procedure for the synthesis of 6a, starting from 21b (80 mg, 0.25 mmol). The crude product was washed with acetonitrile to yield 6c as a white powder HCl salt (55 mg, 90%). $^1$H NMR (500 MHz, CD$_3$OD) δ 6.60 (d, J=1.9 Hz, 1H), 4.93 (td, J=6.5, 4.1 Hz, 1H), 4.54 (ddt, J=6.2, 2.3, 1.3 Hz, 1H), 3.32-3.30 (m, 1H, overlapped with solvent peak), 3.07 (ddt, J=17.9, 4.1, 1.5 Hz, 1H). $^{13}$C NMR (126 MHz, CD$_3$OD) δ 166.0, 142.5, 135.5, 59.3, 49.3 (overlapped with solvent peak), 42.8. HRMS (ESI) calcd for C$_6$H$_9$BrNO$_2$ [M+H]$^+$: 205.9811; found, 205.9808.

Molecular Docking Protocol. Docking models of ligands bound to GABA-AT were developed using the Molecular Operating Environment (MOE) computational suite's Builder utility.[3-5] The energy minimization of ligands was conducted in the gas phase using the force field MMFF94X, followed by the Conformational Search protocol to generate structural-conformation databases. The X-ray crystal structures of native GABA-AT (PDB code 1OHV) and inactivated GABA-AT (PDB code 4Y0I) were uploaded to MOE, followed by the Receptor Preparation step. The tight-binding product in the active pocket was deleted, and catalytic Lys329 was neutralized. The docking site was specified by the Lys329-PLP linkage. Ligand docking simulation was carried out in the prepared aminotransferase enzyme models with unrelated substrates and the solvent atoms inactivated. Ligand placement employed the Alpha Triangle method with Affinity dG scoring generating 300 data points that were further refined using the induced fit method with GBVI/WSA dG scoring to obtain the top 50 docking results. The docking results of each ligand were analyzed for selection of the best docking pose, based on the score and reported X-ray structures. All renderings were then performed in PyMOL.

Figure 5:
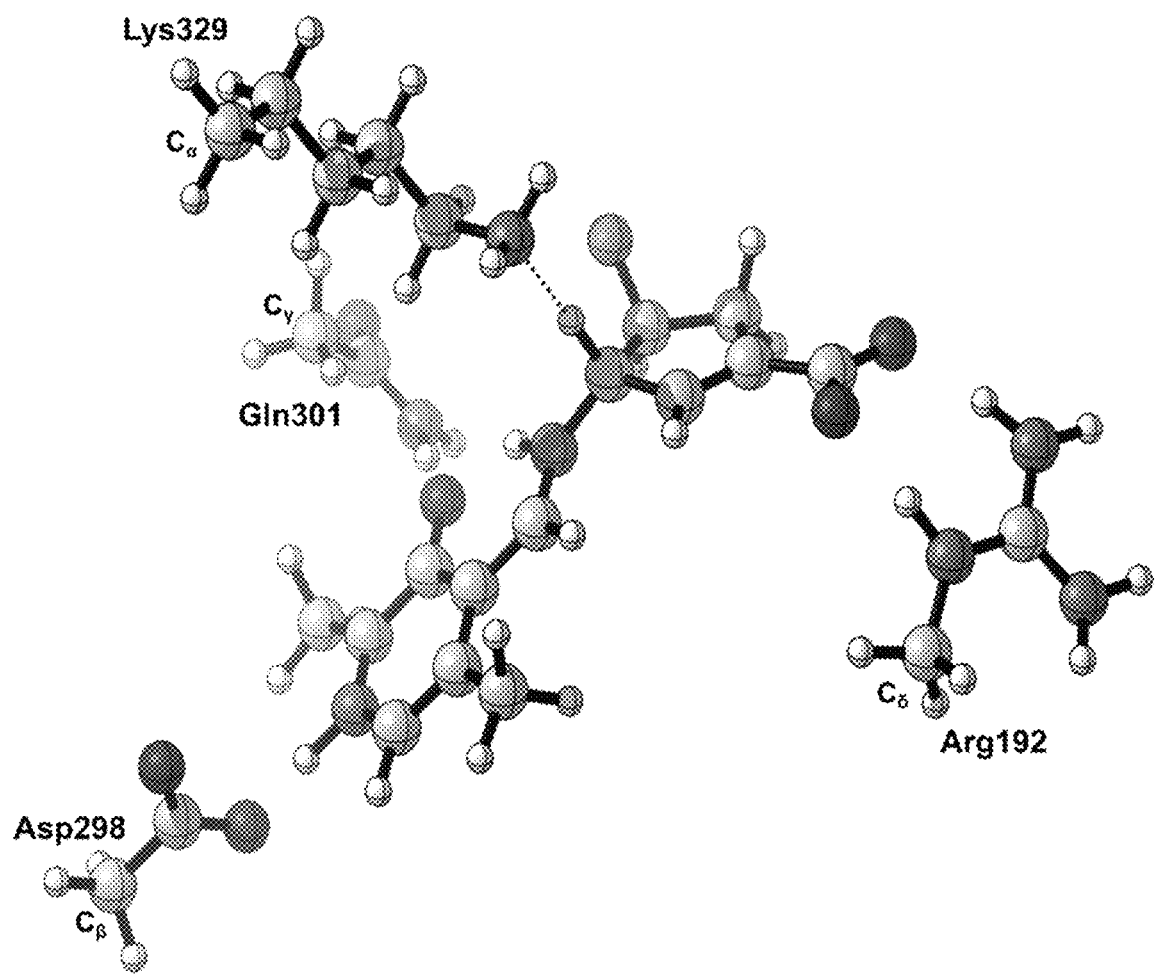
FIG. 5. Cluster model of the M1/M1' bound enzyme active site.
Figure 6:
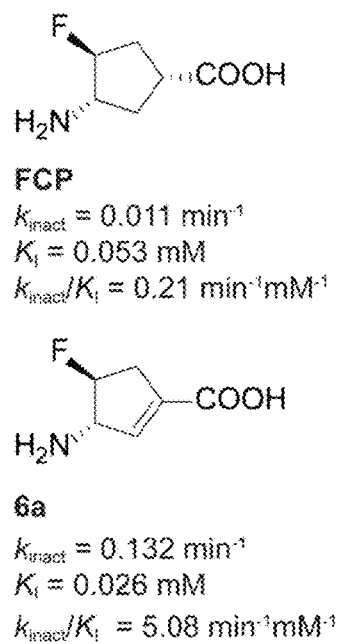
Figure 6:
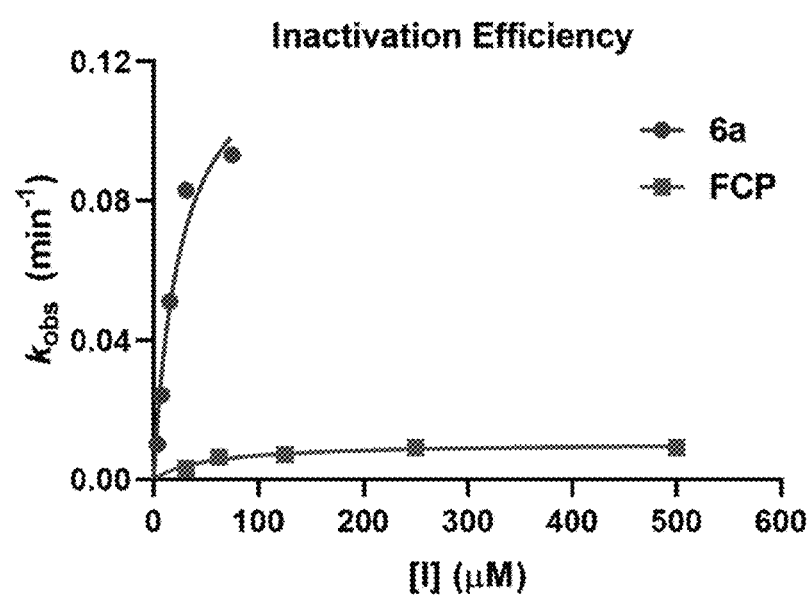
Figure 7:
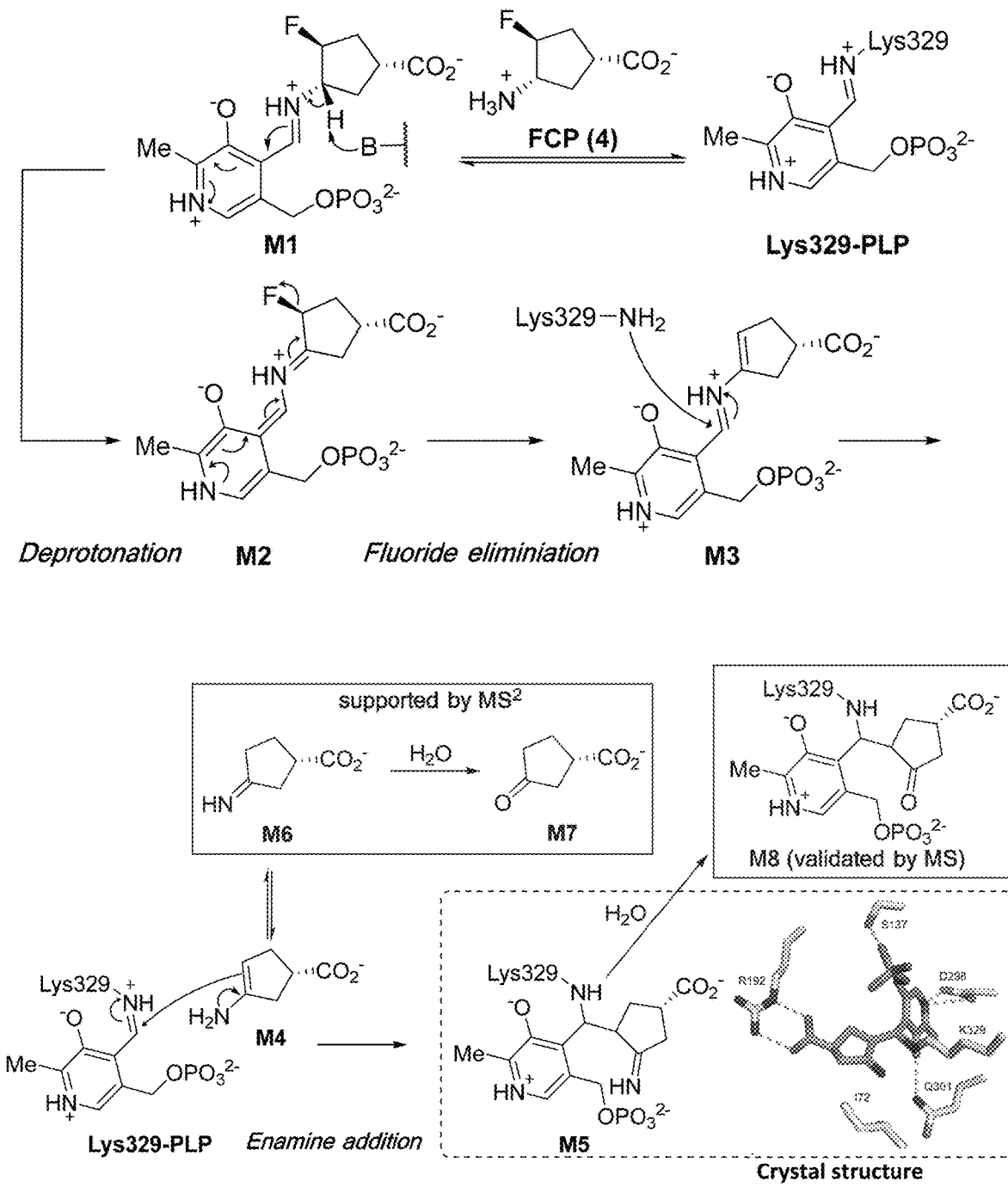

Quantum Mechanical Cluster Calculations. The cluster model of the M1/M1' bound enzyme active site was constructed from the corresponding docking poses, which include Arg192, Lys329, Gln301, and Asp298 amino acids truncated at Cδ, Cα, Cγ, and Cβ atoms, respectively. (See FIG. 5). To further simplify the model, the phosphate groups of M1 and MV were replaced with methyl groups. MV is represented in the Figure below. All geometries involved in the deprotonation steps were optimized at the B3LYP/6-31+G(d,p) level of theory in aqueous medium while the positions of the Cδ, Cα, Cγ, and Cβ atoms of the amino acids residues were kept fixed relative to each other. This procedure is essential to prevent unrealistic movements of the interacting residues of the active site cluster model. Vibrational analyses were performed on the optimized geometries to confirm the minima corresponding to reactants and products (absence of prominent imaginary frequency) as well as the first-order saddle point corresponding to the transition state (presence of one prominent imaginary frequency corresponding). Frozen atoms of the cluster model led to a few small imaginary frequencies all below 30 cm$^{-1}$. However, the contribution of these frequencies to the zero-point energy (ZPE) are insignificant and can be ignored. Intrinsic Reaction Coordinate (IRC) calculations were carried out to further characterize the transition state structures and to confirm that these structures connect with the reactants and products.

Enzyme Assays. GABA-AT was isolated from pig brains and purified according to a literature procedure.[8] Coupled enzyme assays for GABA-AT, Orn-AT, Ala-AT, and Asp-AT were carried out according to previous procedures.[9,10]

Dialysis Assay. The dialysis experiment was conducted using previous protocols.[9,11,12]

Partition Ratio Experiment. The partition ratio was calculated using previous protocols.[9,11,12]

Fluoride Ion Release Assay. The fluoride ion release assay was conducted using previous protocols.[9] The final concentration of enzyme in the sample was determined via BCA protein assay kit (Pierce, cat: 23225). A calibration curve of voltage (V, mV) was generated from varying concentrations of NaF (F, μM). For accurate detection of fluoride ion concentration, 10 μM of fluoride ion was added to each control and sample. The number of fluoride ions released per active site was calculated by the ratio of the fluoride ion release concentration and enzyme concentration.

Intact Protein and Small Molecule Mass Spectrometry. Treated and unmodified purified GABA-AT samples were desalted ten times with Optima-grade water (Fisher) on Amicon Ultra 30 kDa molecular weight spin filters (Millipore). To chromatographically resolve protein, 0.5 μg of protein was loaded onto a 3 cm PLRP-S (Agilent) trap column using a Dionex Ultimate3000 liquid chromatography system (Thermo Fisher). The protein analyte was washed with a 10-min isocratic gradient of 10% Solvent B (95% acetonitrile/5% H$_2$O/0.2% formic acid) and 90% Solvent A (5% acetonitrile/95% H$_2$O/0.2% formic acid). Protein was resolved on an in-house made 75 μm ID×15 cm long nanopore capillary column packed with PLRP-S resin (Agilent). The LC system was operated at a flow rate of 0.3 μL/min at the following gradient: 0-10 min 10% Solvent B; 10-12 min to 40% Solvent B; 12-22 min to 90% Solvent B; 22-24 min at 90% Solvent B; 24-26 min to 10% Solvent B; 26-30 min isocratic at 10% Solvent B. Positive, full-profile ESI data were acquired in the Orbitrap mass analyzers on a Fusion Lumos Tribrid mass spectrometer (Thermo Fisher) operated in low pressure, protein mode, with a [M+24H$^+$]$^{+24}$ default charge state. A custom nano-electrospray ionization source was used with a static spray voltage of 1,700 V. Data were collected in a 500-2,000 m/z window, averaging 20 microscans per scan event at a resolving power of 7,500 at (200 m/z) with a maximum injection time of 50 ms and a target value for the automatic gain control (AGC) of 5e6 charges. Averaged summed scans were manually deconvoluted to generate neutral masses. Small molecule and metabolite masses were identified and characterized by positive and negative mode high-resolution LC-MS/MS on a Q-Exactive Orbitrap mass spectrometer (Thermo) as previously described.[11]

REFERENCES

1. Storici, P.; Qiu, J.; Schirmer, T.; Silverman, R. B., Mechanistic crystallography. Mechanism of inactivation of gamma-aminobutyric acid aminotransferase by (1R, 3S,4S)-3-amino-4-fluorocyclopentane-1-carboxylic acid as elucidated by crystallography. *Biochemistry* 2004, 43, 14057-14063.
2. Lu, H.; Silverman, R. B., Fluorinated conformationally restricted gamma-aminobutyric acid aminotransferase inhibitors. *J. Med. Chem.* 2006, 49, 7404-7412.
3. Heath, T. K.; Lutz, M. R.; Reidl, C. T.; Guzman, E. R.; Herbert, C. A.; Nocek, B. P.; Holz, R. C.; Olsen, K. W.; Ballicora, M. A.; Becker, D. P., Practical spectrophotometric assay for the dapE-encoded N-succinyl-L, L-diaminopimelic acid desuccinylase, a potential antibiotic target. *Plos One* 2018, 13.
4. Vilar, S.; Cozza, G.; Moro, S., Medicinal chemistry and the molecular operating environment (MOE): application of QSAR and molecular docking to drug discovery. *Curr. Top. Med. Chem.* 2008, 8, 1555-1572.
5. Boyd, S., Molecular operating environment. *Chem. World-Uk* 2005, 2, 66.
6. Christensen, E. M.; Patel, S. M.; Korasick, D. A.; Campbell, A. C.; Krause, K. L.; Becker, D. F.; Tanner, J. J., Resolving the cofactor-binding site in the proline biosynthetic enzyme human pyrroline-5-carboxylate reductase 1. *J. Biol. Chem.* 2017, 292, 7233-7243.
7. Mascarenhas, R.; Le, H. V.; Clevenger, K. D.; Lehrer, H. J.; Ringe, D.; Kelleher, N. L.; Silverman, R. B.; Liu, D., Selective targeting by a mechanism-based inactivator against pyridoxal 5'-phosphate-dependent enzymes: mechanisms of inactivation and alternative turnover. *Biochemistry* 2017, 56, 4951-4961.
8. Churchich, J. E.; Moses, U., 4-Aminobutyrate aminotransferase—the presence of nonequivalent binding-sites. *J. Biol. Chem.* 1981, 256, 1101-1104.
9. Lee, H.; Doud, E. H.; Wu, R.; Sanishvili, R.; Juncosa, J. I.; Liu, D. L.; Kelleher, N. L.; Silverman, R. B., Mechanism of inactivation of gamma-aminobutyric acid aminotransferase by (1S,3S)-3-amino-4-difluoromethylene-1-cyclopentanoic acid (CPP-115). *J. Am. Chem. Soc.* 2015, 137, 2628-2640.
10. Juncosa, J. I.; Lee, H.; Silverman, R. B., Two continuous coupled assays for ornithine-delta-aminotransferase. *Anal. Biochem.* 2013, 440, 145-149.
11. Moschitto, M. J.; Doubleday, P. F.; Catlin, D. S.; Kelleher, N. L.; Liu, D.; Silverman, R. B., Mechanism of inactivation of ornithine aminotransferase by (1S,3S)-3-amino-4-(hexafluoropropan-2-ylidenyl)cyclopentane-1-carboxylic acid. *J. Am. Chem. Soc.* 2019, 141, 10711-10721.
12. Juncosa, J. I.; Takaya, K.; Le, H. V.; Moschitto, M. J.; Weerawarna, P. M.; Mascarenhas, R.; Liu, D. L.; Dewey, S. L.; Silverman, R. B., Design and mechanism of (S)-3-amino-4-(difluoromethylenyl)cyclopent-1-ene-1-carboxylic acid, a highly potent gamma-aminobutyric acid aminotransferase inactivator for the treatment of addiction. *J. Am. Chem. Soc.* 2018, 140, 2151-2164.

Example 3

Aminotransferases are pyridoxal 5'-phosphate-dependent enzymes that catalyze reversible transamination reactions between an amino acid and an α-keto acid, playing a critical role in cellular nitrogen metabolism. It is evident that γ-aminobutyric acid aminotransferase (GABA-AT), which balances the levels of inhibitory and excitatory neurotransmitters, is emerging as a promising therapeutic target for epilepsy and cocaine addiction based on mechanism-based inactivators (MBIs). In this work, we established an integrated approach using computational simulation, organic synthesis, biochemical evaluation, and mass spectrometry to facilitate our design and mechanistic studies of MBIs, which led to the identification of a novel cyclopentene-based analogue (6a), 25-times more efficient as an inactivator of GABA-AT compared to the parent compound (1R,3S,4S)-3-amino-4-fluorocyclopentane carboxylic acid (FCP).

Kinetic constant results and PK profiles are shown in Table 3.

TABLE 3

| Compound | Route | Dose (mg/kg) | Tmax (hr) | $^aC_0/C_{max}$ (ng/mL) | $AUC_{last}$ (hr*ng/mL) | $AUC_{inf}$ (hr*ng/ml) | $T_{1/2}$ (hr) | CL (mL/min/kg) | Vss (L/kg) | % $F^b$ |
|---|---|---|---|---|---|---|---|---|---|---|
| SS-1-202 | IV | 10 | — | 6195.82 | 1916.62 | 1968.30 | 0.19 | 84.68 | 1.30 | — |
| | PO | 30 | 0.50 | 4991.45 | 5580.22 | 5810.65 | — | — | — | 97 | a — back extrapolated conc. for IV group; b — $AUC_{last}$ considered for calculating the bioavailability

| | GABA-AT | | | OAT | | |
|---|---|---|---|---|---|---|
| Compound | $K_{inact}(min^{-1})$ | $K_I(mM)$ | $K_{inact}/K_I$ $(min^{-1}mM^{-1})$ | $K_{inact}(min^{-1})$ | $K_I(mM)$ | $K_{inact}/K_I$ $(min^{-1}mM^{-1})$ |
| FCP | 0.011 ± 0.001 | 0.053 ± 0.022 | 0.20 | 0.086 ± 0.010 | 1.40 ± 0.41 | 0.06 |
| 6a | 0.132 ± 0.023 | 0.026 ± 0.011 | 5.08 | 0.143 ± 0.014 | 0.25 ± 0.06 | 0.56 |
| 6b | 0.135 ± 0.010 | 6.01 ± 0.89 | 0.022 | 0.293 ± 0.051 | 2.34 ± 0.66 | 0.13 |
| 6c | 0.086 ± 0.011 | 14.26 ± 3.94 | 0.006 | 0.156 ± 0.020 | 1.29 ± 0.319 | 0.12 |
| Vigabatrin (1) | 0.211 | 0.29 | 0.727 | | N/Db | |
| Bis(CF)$_3$ | | N/D | | 0.094 | 0.091 | 1.03 |

As Table 3 shows, compound 6a (SS-1-202) shows comparable potency with CPP-115 and OV329 which are in the clinical/preclinical stage. Compound 6a (SS-1-202) displays improved inactivation efficiency relative to the parental compound (1 R,3S,4S)-3-amino-4-fluorocyclopentane carboxylic acid (FCP) and vigabatrin. Compound 6a (SS-1-202) is selective over Asp-AT and Ala-AT. Compound 6a (SS-1-202) shows excellent PK profiles.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound having the following formula, a zwitterion form thereof, or a salt form thereof:

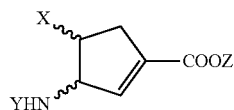

(I)

wherein:
X is halo or hydroxyl;
Y is hydrogen or an amino-protecting group; and
Z is hydrogen, alkyl, or a carboxyl protecting group.

2. The compound of claim 1 having a formula:

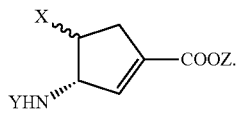

3. The compound of claim 1 having a formula:

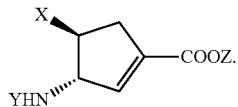

4. The compound of claim 1 having a formula:

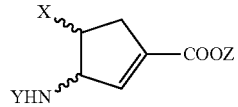

wherein Z is the carboxyl protecting group.

5. The compound of claim 1 having a formula:

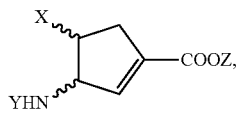

wherein Y is the amino-protecting group.

6. The compound of claim 1 having a formula selected from:

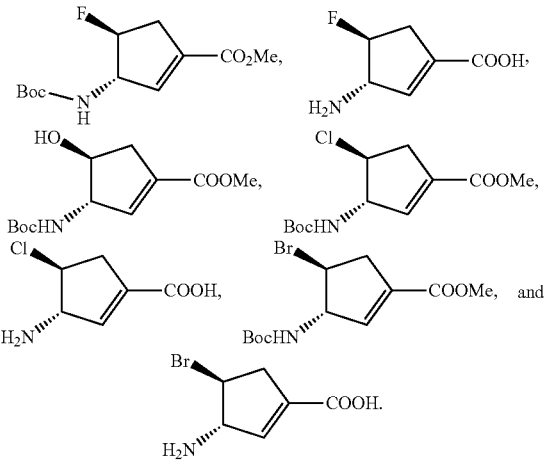

7. The compound of claim 1 in a salt form having a counter ion that is the conjugate base of a protic acid.

8. A pharmaceutical composition comprising the compound of claim 1 or pharmaceutically acceptable salts thereof in a pharmaceutically acceptable carrier.

9. The compound of claim 1, wherein the halo is F, Cl, Br, or I.

10. The compound of claim 4, wherein the carboxyl protecting group is alkyl optionally substituted with aryl, aryl optionally substituted with alkyl, or silyl.

11. The compound of claim 10, wherein the carboxyl protecting group is selected from methyl, tert-butyl, benzyl, 2,6-dimethylphenyl, 2,6-diisopropylphenyl, and 2,6-di-tert-butylphenyl.

12. The compound of claim 5, wherein the amino-protecting group is selected from tert-butoxylcarbonyl (Boc), 9-fluorenylmethoxcarbonyl (FMoc), benzyloxycarbonyl or carboxybenzyl or carbobenzyloxy (Cbz), acetyl (Ac), trifluoroacetyl, phthalic anhydride, benzyl (Bn), benzoyl (Bz), triphenylmethyl (Tr), benzylidenyl, para-toluenesulfonyl (Ts), para-Methoxybenzyl carbonyl (Moz or MeOZ), para-Methoxybenzyl (PMB), 3,4-Dimethoxybenzyl (DMPM), p-methoxyphenyl (PMP), and trichloroethyl chloroformyl (Troc).

13. A method of treating a subject having a disease, disorder, or addiction associated with gamma-aminobutyric acid aminotransferase (GABA-AT) activity, the method comprising administering to the subject the compound of claim 1.

14. The method of claim 13, wherein the subject is administered an amount of the compound sufficient to modulate GABA-AT activity.

15. A method of modulating dopamine levels in a subject in need thereof, the method comprising administering to the subject the compound of claim 1.

16. The method of claim 15, wherein the subject is administered an amount of the compound sufficient to modulate GABA-AT activity.

17. The method of claim 15, wherein the dopamine levels are responsive to ingestion of an addictive substance.

18. The method of claim 15, wherein the method treats excessive dopamine release in the subject.

19. A method for treating substance addiction in a subject in need thereof, the method comprising administering to the subject the compound of claim 1.

20. The method of claim 19, wherein the subject is addicted to a substance selected from the group consisting of cocaine, heroin, alcohol, barbiturates, amphetamines, cannabis, methadone, opioids, stimulants, nicotine, and combinations thereof.

21. A method for treating a neurological or psychological disease or disorder in a subject in need thereof, the method comprising administering to the subject the compound of claim 1.

22. The method of claim 21, wherein the subject is administered an amount of the compound sufficient to modulate GABA-AT activity.

23. The method of claim 21, wherein the disease or disorder is a neurological disorder selected from the group consisting of epilepsy, partial seizures, complex partial seizures, secondary generalized seizures, tonic-clonic seizures, succinic semialdehyde dehydrogenase deficiency (SSADHD), infantile spasms in West's syndrome, Lennox-Gastaut syndrome, tubulous sclerosis, Tourette's syndrome, movement disorders, fibromyalgia, neuropathic pain, migraine related to epilepsy, restless leg syndrome and post-traumatic stress disorder, addiction, obesity, obsessive-compulsive disorders and Alzheimer's disease, and combinations thereof.

24. The method of claim 21, wherein the disease or disorder is a psychological disorder selected from the group consisting of general anxiety disorder, pathological or compulsive gambling disorder, compulsive eating, body dysmorphic disorder, hypochondriasis, pathologic grooming conditions, kleptomania, pyromania, attention deficit hyperactivity disorder and impulse control disorders and combinations thereof.

25. A method of treating a subject having a disease or disorder associated with ornithine aminotransferase (OAT) activity, the method comprising administering to the subject the compound of claim 1.

26. The method of claim 25, wherein the subject is administered an amount of the compound sufficient to modulate OAT activity.

27. The method of claim 25, wherein the method reduces OAT activity and glutamate production characterized by OAT activity.

28. The method of claim 25, wherein the disease or disorder is hepatocellular carcinoma (HCC), non-small cell lung cancer (NSCLC), or other diseases that involve overexpression of OAT.

\* \* \* \* \*